(12) United States Patent
Himmelsbach et al.

(10) Patent No.: US 6,617,329 B2
(45) Date of Patent: Sep. 9, 2003

(54) AMINOQUINAZOLINES AND THEIR USE AS MEDICAMENTS

(75) Inventors: Frank Himmelsbach, Mittelbiberach (DE); Elke Langkopf, Warthausen (DE); Birgit Jung, Schwabenheim (DE); Stefan Blech, Warthausen (DE); Flavio Solca, Wien (AT)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/938,314

(22) Filed: Aug. 23, 2001

(65) Prior Publication Data

US 2002/0049197 A1 Apr. 25, 2002

Related U.S. Application Data

(60) Provisional application No. 60/230,118, filed on Sep. 5, 2000.

(30) Foreign Application Priority Data

Aug. 26, 2000 (DE) .......................... 100 42 059

(51) Int. Cl.$^7$ .................. C07D 239/94; C07D 405/12; C07D 413/12; A61K 31/517; A61P 35/00
(52) U.S. Cl. .............. 514/252.14; 514/252.15; 514/252.17; 514/227.8; 514/234.8; 514/211.15; 540/596; 544/61; 544/111; 544/115; 544/119; 544/284; 544/293
(58) Field of Search ............... 544/284, 293, 544/111, 61, 115, 119; 540/596; 514/227.8, 234.8, 252.16, 252.15, 252.17, 211.15, 252.14

(56) References Cited

FOREIGN PATENT DOCUMENTS

| | | |
|---|---|---|
| EP | 0 566 226 A1 | 10/1993 |
| EP | 0 787 722 A1 | 8/1997 |
| WO | WO 96 33980 A1 | 10/1996 |
| WO | WO 97 30035 A1 | 8/1997 |
| WO | WO 97 32856 A1 | 9/1997 |
| WO | WO 98 13354 A1 | 4/1998 |
| WO | WO 99 01467 | 1/1999 |
| WO | WO 99 09016 A1 | 2/1999 |
| WO | WO 00 18740 A1 | 4/2000 |
| WO | WO 00 55141 A1 | 9/2000 |

OTHER PUBLICATIONS

Boschelli; "Small molecule inhibitors of receptor tyrosine kinases"; Review Article—Chemical Sciences.

*Primary Examiner*—Mukund J. Shah
*Assistant Examiner*—Venkataraman Balasubramanian
(74) *Attorney, Agent, or Firm*—Robert P. Raymond; Alan R. Stempel; Mary-Ellen M. Devlin

(57) ABSTRACT

Compounds of the formula

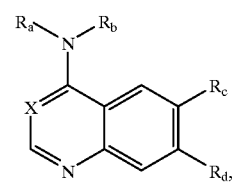

(I)

having an inhibitory effect on signal transduction mediated by tyrosine kinases, their use in the treatment of diseases, especially tumoral diseases and diseases of the lungs and air-ways, and the preparation thereof.

8 Claims, No Drawings

AMINOQUINAZOLINES AND THEIR USE AS MEDICAMENTS

RELATED APPLICATIONS

Benefit of U.S. Provisional Application Serial No. 60/230,118, filed on Sep. 5, 2000 is hereby claimed.

DESCRIPTION OF THE INVENTION

The present invention relates to bicyclic heterocycles of general formula

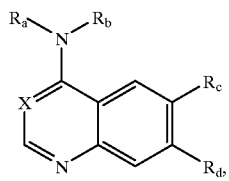

(I)

the tautomers, the stereoisomers and the salts thereof, particularly the physiologically acceptable salts thereof with inorganic or organic acids or bases which have valuable pharmacological properties, particularly an inhibitory effect on signal transduction mediated by tyrosine kinases, the use thereof for treating diseases, particularly tumoral diseases, diseases of the lungs and respiratory tract, and the preparation thereof.

In the above general formula I

X denotes a methyne group substituted by a cyano group or a nitrogen atom, $R_a$ denotes a hydrogen atom or a methyl group, $R_b$ denotes a phenyl, benzyl or 1-phenylethyl group, wherein the phenyl nucleus in each case is substituted by the groups $R_1$ to $R_3$, where $R_1$ and $R_2$, which may be identical or different, each denote a hydrogen, fluorine, chlorine, bromine or iodine atom, a methyl, ethyl, hydroxy, methoxy, ethoxy, amino, cyano, vinyl or ethynyl group, an aryl, aryloxy, arylmethyl or arylmethoxy group, a methyl or methoxy group substituted by 1 to 3 fluorine atoms or $R_1$ together with $R_2$, if they are bound to adjacent carbon atoms, denotes a —CH=CH—CH=CH, —CH=CH—NH or —CH=N—NH group and $R_3$ denotes a hydrogen, fluorine, chlorine or bromine atom, one of the groups $R_c$ or $R_d$ denotes an —A—B group and the other group $R_c$ or $R_d$ denotes a —C—D group, where A denotes a $C_{1-6}$-alkylene group, a —O—$C_{1-6}$-alkylene group, where the alkylene moiety is linked to the group B, or an oxygen atom, while this may not be linked to a nitrogen atom of the group B, and B denotes a pyrrolidino group wherein the two hydrogen atoms in the 2 position are replaced by a group E, wherein E represents a —CH$_2$—O—CO—CH$_2$, —CH$_2$CH$_2$—O—CO, —CH$_2$—O—CO—CH$_2$CH$_2$, —CH$_2$CH$_2$—O—CO—CH$_2$ or —CH$_2$CH$_2$CH$_2$—O—CO— bridge optionally substituted by one or two $C_{1-2}$-alkyl groups, a pyrrolidino group wherein the two hydrogen atoms in the 3 position are replaced by a group F wherein F denotes an —O—CO—CH$_2$CH$_2$, —CH$_2$—O—CO—CH$_2$, —CH$_2$CH$_2$—O—CO, —O—CO—CH$_2$CH$_2$CH$_2$, —CH$_2$—O—CO—CH$_2$CH$_2$, —CH$_2$CH$_2$—O—CO—CH$_2$, —CH$_2$CH$_2$CH$_2$—O—CO, —O—CO—CH$_2$—NR$_4$—CH$_2$, —CH$_2$—O—CO—CH$_2$—NR$_4$, —O—CO—CH$_2$—O—CH$_2$ or —CH$_2$—O—CO—CH$_2$—O— bridge optionally substituted by one or two $C_{1-2}$-alkyl groups, where $R_4$ denotes a hydrogen atom or a $C_{1-4}$-alkyl group, a piperidino or hexahydroazepino group, wherein the two hydrogen atoms in the 2 position are replaced by a group E, where E is as hereinbefore defined, a piperidino or hexahydroazepino group, wherein in each case the two hydrogen atoms in the 3 position or in the 4 position are replaced by a group F, where F is as hereinbefore defined, a piperazino or 4-($C_{1-4}$-alkyl)-piperazino group, wherein the two hydrogen atoms in the 2 position or in the 3 position of the piperazino ring are replaced by a group E, where E is as hereinbefore defined, a pyrrolidino or piperidino group, wherein two neighbouring hydrogen atoms are replaced by a —O—CO—CH$_2$, —CH$_2$—O—CO, —O—CO—CH$_2$CH$_2$, —CH$_2$—O—CO—CH$_2$, —CH$_2$CH$_2$—O—CO, —O—CO—CH$_2$—NR$_4$ or —O—CO—CH$_2$—O— bridge optionally substituted by one or two $C_{1-2}$-alkyl groups, where $R_4$ is as hereinbefore defined and the heteroatoms of the abovementioned bridges are not bound to the 2 or 5 position of the pyrrolidino ring and are not bound to the 2 or 6 position of the piperidino ring, a piperazino or 4-($C_{1-4}$-alkyl)-piperazino group, wherein a hydrogen atom in the 2 position together with a hydrogen atom in the 3 position of the piperazino ring are replaced by a —CH$_2$—O—CO—CH$_2$ or —CH$_2$CH$_2$—O—CO— bridge optionally substituted by one or two $C_{1-2}$-alkyl groups, a piperazino group wherein a hydrogen atom in the 3 position together with the hydrogen atom in the 4 position are replaced by a —CO—O—CH$_2$CH$_2$ or —CH$_2$—O—CO—CH$_2$— bridge optionally substituted by one or two $C_{1-2}$-alkyl groups, where in each case the left-hand end of the abovementioned bridges is bound to the 3 position of the piperazino ring, a pyrrolidino, piperidino or hexahydroazepino group substituted by the group $R_5$ wherein $R_5$ represents a 2-oxo-tetrahydrofuranyl, 2-oxo-tetrahydropyranyl, 2-oxo-1,4-dioxanyl or 2-oxo-4-($C_{1-4}$-alkyl)-morpholinyl group optionally substituted by one or two $C_{1-2}$-alkyl groups, a pyrrolidino group substituted in the 3 position by a 2-oxo-morpholino group, while the 2-oxo-morpholino group may be substituted by one or two $C_{1-2}$-alkyl groups, a piperidino or hexahydroazepino group substituted in the 3 or 4 position by a 2-oxo-morpholino group, while the 2-oxo-morpholino group may be substituted by one or two $C_{1-2}$-alkyl groups, a 4-($C_{1-4}$-alkyl)-piperazino or 4-($C_{1-4}$-alkyl)-homopiperazino group substituted at a cyclic carbon atom by $R_5$, wherein $R_5$ is as hereinbefore defined, a piperazino or homopiperazino group substituted in the 4 position by the group $R_6$, wherein $R_6$ represents a 2-oxo-tetrahydrofuran-3-yl, 2-oxo-tetrahydrofuran-4-yl, 2-oxo-tetrahydropyran-3-yl, 2-oxo-tetrahydropyran-4-yl or 2-oxo-tetrahydropyran-5-yl group optionally substituted by one or two $C_{1-2}$-alkyl groups, a pyrrolidino group substituted in the 3 position by an ($R_4NR_6$), $R_6O$, $R_6S$, $R_6SO$ or $R_6SO_2$ group, where $R_4$ and $R_6$ are as hereinbefore defined, a piperidino or hexahydroazepino group substituted in the 3 or 4 position by an ($R_4NR_6$), ($R_6O$, $R_6S$, $R_6SO$ or $R_6SO_2$ group, wherein $R_4$ and $R_6$ are as hereinbefore defined, a pyrrolidino, piperidino or hexahydroazepino group substituted by an $R_5$—$C_{1-4}$-alkyl, $R_4NR_6$)—$C_{1-4}$-alkyl, $R_6O$—

$C_{1-4}$-alkyl, $R_6S$—$C_{1-4}$-alkyl, $R_6SO$—$C_{1-4}$-alkyl, $R_6SO_2$—$C_{1-4}$-alkyl or $R_4NR_6$—CO group, wherein $R_4$ to $R_6$ are as hereinbefore defined, a pyrrolidino group substituted in the 3 position by an $R_5$—CO—$NR_4$, $R_5$—$C_{1-4}$-alkylene-$CONR_4$, $(R_4NR_6)$—$C_{1-4}$-alkylene-$CONR_4$, $R_6O$—$C_{1-4}$-alkylene-$CONR_4$, $R_6S$—$C_{1-4}$-alkylene-$CONR_4$, $R_6SO$—$C_{1-4}$-alkylene-$CONR_4$, $R_6SO_2$—$C_{1-4}$-alkylene-$CONR_4$, 2-oxo-morpholino-$C_{1-4}$-alkylene-$CONR_4$, $R_5$—$C_{1-4}$-alkylene-Y or $C_{2-4}$-alkyl-Y group, where the $C_{2-4}$-alkyl moiety of the $C_{2-4}$-alkyl-Y group in each case is substituted from position 2 by an $(R_4NR_6)$, $R_6O$, $R_6S$, $R_6SO$ or $R_6SO_2$ group and the 2-oxo-morpholino moiety may be substituted by one or two $C_{1-2}$-alkyl groups, wherein $R_4$ to $R_6$ are as hereinbefore defined and Y represents an oxygen or sulphur atom, an imino, N—$(C_{1-4}$-alkyl)-imino, sulphinyl or sulphonyl group, a piperidino or hexahydroazepino group substituted in the 3 or 4 position by an $R_5$—CO—$NR_4$, $R_5$—$C_{1-4}$-alkylene-$CONR_4$, $(R_4NR_6)$—$C_{1-4}$-alkylene-$CONR_4$, $R_6O$—$C_{1-4}$-alkylene-$CONR_4$, $R_6S$—$C_{1-4}$-alkylene-$CONR_4$, $R_6SO$—$C_{1-4}$-alkylene-$CONR_4$, $R_6SO_2$—$C_{1-4}$-alkylene-$CONR_4$, 2-oxo-morpholino-$C_{1-4}$-alkylene-$CONR_4$, $R_5$—$C_{1-4}$-alkylene-Y or $C_{2-4}$-alkyl-Y group, wherein Y is as hereinbefore defined, the 2-oxo-morpholino moiety may be substituted by one or two $C_{1-2}$-alkyl groups and the $C_{2-4}$-alkyl moiety of the $C_{2-4}$-alkyl-Y group is substituted in each case from position 2 by an $(R_4NR_6)$, $R_6O$, $R_6S$, $R_6SO$ or $R_6SO_2$ group, where $R_4$ to $R_6$ are as hereinbefore defined, a 4-($C_{1-4}$-alkyl)-piperazino or 4-($C_{1-4}$-alkyl)-homopiperazino group substituted at a cyclic carbon atom by an $R_5$—$C_{1-4}$-alkyl, $(R_4NR_6)$—$C_{1-4}$-alkyl, $R_6O$—$C_{1-4}$-alkyl, $R_6S$—$C_{1-4}$-alkyl, $R_6SO$—$C_{1-4}$-alkyl, $R_6SO_2$—$C_{1-4}$-alkyl or $R_4NR_6$—CO group, wherein $R_4$ to $R_6$ are as hereinbefore defined, a piperazino or homopiperazino group substituted in the 4 position by an $R_5$—$C_{1-4}$-alkyl, $R_5$—CO, $R_5$—$C_{1-4}$-alkylene-CO, $(R_4NR_6)$—$C_{1-4}$-alkylene-CO, $R_6O$—$C_{1-4}$-alkylene-CO, $R_6S$—$C_{1-4}$-alkylene-CO, $R_6SO$—$C_{1-4}$-alkylene-CO or $R_6SO_2$—$C_{1-4}$-alkylene-CO group, wherein $R_4$ to $R_6$ are as hereinbefore defined, a piperazino or homopiperazino group substituted in the 4 position by a $C_{2-4}$-alkyl group, wherein the $C_{2-4}$-alkyl group is substituted in each case from position 2 by an $(R_4NR_6)$, $R_6O$, $R_6S$, $R_6SO$ or $R_6SO_2$ group, where $R_4$ and $R_6$ are as hereinbefore defined, a pyrrolidino, piperidino or hexahydroazepino group substituted by a 2-oxo-morpholino-$C_{1-4}$-alkyl group, wherein the 2-oxo-morpholino moiety may be substituted by one or two $C_{1-2}$-alkyl groups, a pyrrolidino group substituted in the 3 position by a $C_{2-4}$-alkyl-Y group, wherein Y is as hereinbefore defined and the $C_{2-4}$-alkyl moiety of the $C_{2-4}$-alkyl-Y group is substituted in each case from position 2 by a 2-oxo-morpholino group optionally substituted by one or two $C_{1-2}$-alkyl groups, a piperidino or hexahydroazepino group substituted in the 3 or 4 position by a $C_{2-4}$-alkyl-Y group, wherein Y is as hereinbefore defined and the $C_{2-4}$-alkyl moiety of the $C_{2-4}$-alkyl-Y group is substituted in each case from position 2 by a 2-oxo-morpholino group optionally substituted by one or two $C_{1-2}$-alkyl groups, a 4-($C_{1-4}$-alkyl)-piperazino or 4-($C_{1-4}$-alkyl)-homopiperazino group substituted at a cyclic carbon atom by a 2-oxo-morpholino-$C_{1-4}$-alkyl group, wherein the 2-oxo-morpholino moiety may be substituted by one or two $C_{1-2}$-alkyl groups, a piperazino or homopiperazino group substituted in the 4 position by a 2-oxo-morpholino-$C_{1-4}$-alkylene-CO group, wherein the 2-oxo-morpholino moiety may be substituted by one or two $C_{1-2}$-alkyl groups, a piperazino or homopiperazino group substituted in the 4 position by a $C_{2-4}$-alkyl group, wherein the $C_{2-4}$-alkyl moiety is substituted in each case from position 2 by a 2-oxo-morpholino group optionally substituted by one or two $C_{1-2}$-alkyl groups, a pyrrolidinyl or piperidinyl group substituted in the 1 position by the group $R_6$, by an $R_5$—$C_{1-4}$-alkyl, $R_5$—CO, $R_5$—$C_{1-4}$-alkylene-CO, $(R_4NR_6)$—$C_{1-4}$-alkylene-CO, $R_6O$—$C_{1-4}$-alkylene-CO, $R_6S$—$C_{1-4}$-alkylene-CO, $R_6SO$—$C_{1-4}$-alkylene-CO, $R_6SO_2$—$C_{1-4}$-alkylene-CO or 2-oxo-morpholino-$C_{1-4}$-alkylene-CO group, wherein $R_4$ to $R_6$ are as hereinbefore defined and the 2-oxo-morpholino moiety may be substituted by one or two $C_{1-2}$-alkyl groups, a pyrrolidinyl or piperidinyl group substituted in the 1 position by a $C_{2-4}$-alkyl group, wherein the $C_{2-4}$-alkyl moiety is substituted in each case from position 2 by an $(R_4NR_6)$, $R_6O$, $R_6S$, $R_6SO$, $R_6SO_2$ or 2-oxo-morpholino group, where $R_4$ and $R_6$ are as hereinbefore defined and the 2-oxo-morpholino moiety may be substituted by one or two $C_{1-2}$-alkyl groups, a pyrrolidin-3-yl-$NR_4$, piperidin-3-yl-$NR_4$ or piperidin-4-yl-$NR_4$ group substituted in each case at the cyclic nitrogen atom by the group $R_6$, by an $R_5$—$C_{1-4}$-alkyl, $R_5$—CO, $R_5$—$C_{1-4}$-alkylene-CO, $(R_4NR_6)$—$C_{1-4}$-alkylene-CO, $R_6O$—$C_{1-4}$-alkylene-CO, $R_6S$—$C_{1-4}$-alkylene-CO, $R_6SO$—$C_{1-4}$-alkylene-CO, $R_6SO_2$—$C_{1-4}$-alkylene-CO or 2-oxo-morpholino-$C_{1-4}$-alkylene-CO group, wherein $R_4$ to $R_6$ are as hereinbefore defined and the 2-oxo-morpholino moiety may be substituted by one or two $C_{1-2}$-alkyl groups, a pyrrolidin-3-yl-$NR_4$, piperidin-3-yl-$NR_4$ or piperidin-4-yl-$NR_4$ group substituted in each case at the cyclic nitrogen atom by a $C_{2-4}$-alkyl group, wherein the $C_{2-4}$-alkyl moiety is substituted in each case from position 2 by an $(R_4NR_6)$, $R_6O$, $R_6S$, $R_6SO$, $R_6SO_2$ or 2-oxo-morpholino group, where $R_4$ and $R_6$ are as hereinbefore defined and the 2-oxo-morpholino moiety may be substituted by one or two $C_{1-2}$-alkyl groups, a $R_5$—$C_{1-4}$-alkylene-$NR_4$ group wherein $R_4$ and $R_5$ are as hereinbefore defined, or a $C_{2-4}$-alkyl-$NR_4$ group wherein the $C_{2-4}$-alkyl moiety is substituted in each case from position 2 by an $(R_4NR_6)$, $R_6O$, $R_6S$, $R_6SO$, $R_6SO_2$ or 2-oxo-morpholino group, where $R_4$ and $R_6$ are as hereinbefore defined and the 2-oxo-morpholino moiety may be substituted by one or two $C_{1-2}$-alkyl groups, a 2-oxo-morpholin-4-yl group substituted by the group $R_7$ or by the group $R_7$ and a $C_{1-4}$-alkyl group, where $R_7$ represents a $C_{3-4}$-alkyl, hydroxy-$C_{1-4}$-alkyl, $C_{1-4}$-alkoxy-$C_{1-4}$-alkyl, di-($C_{1-4}$-alkyl)-amino-$C_{1-4}$-alkyl, pyrrolidino-$C_{1-4}$-alkyl, piperidino-$C_{1-4}$-alkyl, morpholino-$C_{1-4}$-alkyl, 4-($C_{1-4}$-alkyl)-piperazino-$C_{1-4}$-alkyl, $C_{1-4}$-alkylsulphanyl-$C_{1-4}$-alkyl, $C_{1-4}$-alkylsulphinyl-$C_{1-4}$-alkyl, $C_{1-4}$-alkylsulphonyl-$C_{1-4}$-alkyl, cyano-$C_{1-4}$-alkyl, $C_{1-4}$-alkoxycarbonyl-$C_{1-4}$-alkyl, aminocarbonyl-$C_{1-4}$-alkyl, $C_{1-4}$-alkyl-aminocarbonyl-$C_{1-4}$-alkyl, di-($C_{1-4}$-alkyl)-aminocarbonyl-$C_{1-4}$-alkyl, pyrrolidinocarbonyl-$C_{1-4}$-alkyl, piperidinocarbonyl-$C_{1-4}$-alkyl, morpholinocarbonyl-$C_{1-4}$-alkyl or a 4-($C_{1-4}$-alkyl)-piperazinocarbonyl-$C_{1-4}$-alkyl group, a 2-oxo-morpholin-4-yl group substituted by two groups $R_7$, where $R_7$ is as hereinbefore defined and the two groups $R_7$ may be identical or different, a 2-oxo-morpholin-4-yl group wherein the two hydrogen atoms of a methylene group are replaced by a —$(CH_2)_m$, —$CH_2$—Y—$CH_2$, —$CH_2$—Y—$CH_2$—$CH_2$, —$CH_2CH_2$—Y—$CH_2CH_2$ or —$CH_2CH_2$—Y—$CH_2CH_2CH_2$— bridge optionally substituted by one or two $C_{1-2}$-alkyl groups, where Y is as hereinbefore defined and m represents the number 2, 3, 4, 5 or 6, a 2-oxo-morpholin-4-yl group wherein a hydrogen atom in the 5 position together with a hydrogen atom in the 6 position is replaced by a —$(CH_2)_n$, —$CH_2$—Y—$CH_2$, —$CH_2$—Y—$CH_2CH_2$ or —$CH_2$—$C_2$—Y—$CH_2$— bridge, where Y is as hereinbefore defined and n denotes the number 2, 3 or 4, or, if C together with D represents a group $R_e$, it may also represent a 2-oxo-morpholin-4-yl group which may be substituted by 1 to 4 $C_{1-2}$-alkyl groups, C denotes an —O—$C_{1-6}$-alkylene group, where the alkylene moiety is linked to the group D, or an oxygen atom, while this may not be linked to a nitrogen atom of the group D, and D denotes an amino group substituted by 2 $C_{1-4}$-alkyl groups wherein the alkyl groups may be identical or different and each alkyl moiety may be substituted from position 2 by a $C_{1-4}$-alkoxy or di-($C_{1-4}$-alkyl)-amino group or by a 4- to 7-membered alkyleneimino group, while in the abovementioned 6- to 7-membered alkyleneimino groups a methylene group in each case may be replaced in the 4 position by an oxygen or sulphur atom or by a sulphinyl, sulphonyl or N—($C_{1-4}$-alkyl)-imino group, a 4- to 7-membered alkyleneimino group optionally substituted by 1 to 4 methyl groups, a 6- to 7-membered alkyleneimino group optionally substituted by 1 or 2 methyl groups where in each case a methylene group in the 4 position is replaced by an oxygen or sulphur atom, by a sulphinyl, sulphonyl or N—($C_{1-4}$-alkyl)-imino group, an imidazolyl group optionally substituted by 1 to 3 methyl groups, a $C_{5-7}$-cycloalkyl group wherein a methylene group is replaced by an oxygen or sulphur atom, by a sulphinyl, sulphonyl or N—($C_{1-4}$-alkyl)-imino group, or C together with D denotes a hydrogen atom, a $C_{1-6}$-alkoxy group optionally substituted from position 2 by a hydroxy or $C_{1-4}$-alkoxy group, a $C_{3-7}$-cycloalkoxy or $C_{3-7}$-cycloalkyl-$C_{1-4}$-alkoxy group, a tetrahydrofuran-3-yloxy, tetrahydropyran-3-yloxy, tetrahydropyran-4-yloxy, tetrahydrofuranylmethoxy or tetrahydropyranylmethoxy group, or a group $R_e$, where $R_e$ denotes a $C_{2-6}$-alkoxy group which is substituted from position 2 by a $C_{4-7}$-cycloalkoxy or $C_{3-7}$-cycloalkyl-$C_{1-3}$-alkoxy group, a $C_{4-7}$-cycloalkoxy or $C_{3-7}$-cycloalkyl-$C_{1-6}$-alkoxy group, wherein the cycloalkyl moiety is substituted in each case by a $C_{1-4}$-alkyl, $C_{1-4}$-alkoxy, di-($C_{1-4}$-alkyl)-amino, pyrrolidino, piperidino, morpholino, piperazino, N—($C_{1-2}$-alkyl)-piperazino, $C_{1-4}$-alkoxy-$C_{1-2}$-alkyl, di-($C_{1-4}$-alkyl)-amino-$C_{1-2}$-alkyl, pyrrolidino-$C_{1-2}$-alkyl, piperidino-$C_{1-2}$-alkyl, morpholino-$C_{1-2}$-alkyl, piperazino-$C_{1-2}$-alkyl or N—($C_{1-2}$-alkyl)-piperazino-$C_{1-2}$-alkyl group, where the abovementioned cycloalkyl moieties may additionally be substituted by a methyl or ethyl group, while, unless stated otherwise, the aryl moieties mentioned in the definition of the abovementioned groups denote a phenyl group which may be mono- or disubstituted by R', while the substituents may be identical or different, and R' represents a fluorine, chlorine, bromine or iodine atom, a $C_{1-2}$-alkyl, trifluoromethyl or $C_{1-2}$-alkoxy group, or two groups R', if they are bound to adjacent carbon atoms, together denote a $C_{3-4}$-alkylene, methylenedioxy or 1,3-butadien-1,4-ylene group.

Preferred compounds of the above general formula I are those wherein

X denotes a nitrogen atom, $R_a$ denotes a hydrogen atom, $R_b$ denotes a 1-phenylethyl, 3-methylphenyl, 3-chlorophenyl, 3-bromophenyl or 3-chloro-4-fluorophenyl group, $R_c$ denotes an —A—B group wherein A denotes a —$OCH_2CH_2$, —$OCH_2CH_2CH_2$ or —$OCH_2CH_2CH_2CH_2$ group, where the alkylene moiety in each case is linked to the group B, and B denotes a piperidino group wherein the two hydrogen atoms in the 4 position are replaced by a —$CH_2$—O—CO—$CH_2$, —$CH_2CH_2$—O—CO, —$CH_2CH_2$—O—CO—$CH_2$, —O—CO—$CH_2$—$NCH_3$—$CH_2$ or —O—CO—$CH_2$—O—$CH_2$— bridge, a piperazino group wherein a hydrogen atom in the 3 position together with the hydrogen atom in the 4 position are replaced by a —CO—O—$CH_2$—$CH_2$ or —$CH_2$—O—CO—$CH_2$— bridge, where in each case the left-hand end of the abovementioned bridges is bound to the 3 position of the piperazino ring, a piperidino group which is substituted in the 4 position by a 2-oxo-morpholino or 2-oxo-morpholino methyl group, where the 2-oxo-morpholino moiety may be substituted in each case by one or two methyl groups, a piperazino group which is substituted in the 4 position by a 2-oxo-tetrahydrofuran-3-yl or 2-oxo-tetrahydrofuran-4-yl group, a piperidino group which is substituted in the 4 position by an $R_6S$ group, where $R_6$ denotes a 2-oxo-tetrahydrofuran-3-yl or 2-oxo-tetrahydrofuran-4-yl group, a piperazino group which is substituted in the 4 position by a 2-oxo-tetrahydrofuranylmethyl or 2-oxo-tetrahydrofuranylcarbonyl group, a piperazino group which is substituted in the 4 position by a [2-(2-oxo-tetrahydrofuran-3-ylsulphenyl)ethyl] group, a piperidin-4-yl group which is substituted in the 1 position by a 2-oxo-tetrahydrofuran-3-yl or 2-oxo-tetrahydrofuran-4-yl group, a 2-oxo-morpholin-4-yl group which is substituted by a methoxymethyl or methoxyethyl group, a 2-oxo-morpholin-4-yl group wherein the two hydrogen atoms of a methylene group are replaced by a —$CH_2CH_2CH_2CH_2$, —$CH_2CH_2CH_2CH_2CH_2$, —$CH_2$—O—$CH_2CH_2$ or —$CH_2CH_2$—O—$CH_2CH_2$— bridge, and $R_d$ represents a methoxy, cyclopropylmethoxy, tetrahydrofuran-3-yloxy, tetrahydropyran-3-yloxy, tetrahydropyran-4-yloxy, tetrahydrofuranylmethoxy or tetrahydropyranylmethoxy group, the tautomers, stereoisomers and the salts thereof.

Other preferred compounds of the above general formula I are those wherein

X denotes a nitrogen atom, $R_a$ denotes a hydrogen atom, $R_b$ denotes a 1-phenylethyl, 3-methylphenyl, 3-chlorophenyl, 3-bromophenyl or 3-chloro-4-fluorophenyl group, $R_c$ denotes a methoxy, cyclopentyloxy, cyclopropylmethoxy, cyclopentylmethoxy, tetrahydrofuran-3-yloxy, tetrahydropyran-3-yloxy, tetrahydropyran-4-yloxy, tetrahydrofuranylmethoxy or tetrahydropyranylmethoxy group and $R_d$ denotes an —A—B group wherein A denotes an —OCH$_2$CH$_2$, —OCH$_2$CH$_2$CH$_2$ or —OCH$_2$CH$_2$CH$_2$CH$_2$ group, where the alkylene moiety in each case is linked to the group B, and B denotes a piperidino group wherein the two hydrogen atoms in the 4 position are replaced by a —CH$_2$—O—CO—CH$_2$, —CH$_2$CH$_2$—O—CO, —CH$_2$CH$_2$—O—CO—CH$_2$, —O—CO—CH$_2$—NCH$_3$—CH$_2$ or —O—CO—CH$_2$—O—CH$_2$— bridge, a piperazino group wherein a hydrogen atom in the 3 position together with the hydrogen atom in the 4 position are replaced by a —CO—O—CH$_2$—CH$_2$ or —CH$_2$—O—CO—CH$_2$— bridge, where in each case the left-hand end of the abovementioned bridges is bound to the 3 position of the piperazino ring, a piperidino group which is substituted in the 4 position by a 2-oxo-morpholino or 2-oxo-morpholino methyl group, while the 2-oxo-morpholino moiety may be substituted in each case by one or two methyl groups, a piperazino group which is substituted in the 4 position by a 2-oxo-tetrahydrofuran-3-yl or 2-oxo-tetrahydrofuran-4-yl group, a piperidino group which is substituted in the 4 position by an $R_6S$ group, where $R_6$ represents a 2-oxo-tetrahydrofuran-3-yl or 2-oxo-tetrahydrofuran-4-yl group, a piperazino group which is substituted in the 4 position by a 2-oxo-tetrahydrofuranylmethyl or 2-oxo-tetrahydrofuranylcarbonyl group, a piperazino group which is substituted in the 4 position by a [2-(2-oxo-tetrahydrofuran-3-ylsulphenyl)ethyl] group, a piperidin-4-yl group which is substituted in the 1 position by a 2-oxo-tetrahydrofuran-3-yl or 2-oxo-tetrahydrofuran-4-yl group, a 2-oxo-morpholin-4-yl group which is substituted by a methoxymethyl or methoxyethyl group, a 2-oxo-morpholin-4-yl group wherein the two hydrogen atoms of a methylene group are replaced by a —CH$_2$CH$_2$CH$_2$CH$_2$, —CH$_2$CH$_2$CH$_2$CH$_2$CH$_2$, —CH$_2$—O—CH$_2$CH$_2$ or —CH$_2$CH$_2$—O—CH$_2$CH$_2$— bridge, the tautomers, stereoisomers and the salts thereof.

Most particularly preferred compounds of the above general formula I are those wherein X denotes a nitrogen atom, $R_a$ denotes a hydrogen atom, $R_b$ denotes a 3-chloro-4-fluorophenyl group, $R_c$ denotes a cyclopentyloxy, cyclopropylmethoxy, cyclopentylmethoxy, tetrahydrofuran-3-yloxy or tetrahydrofuran-2-yl-methoxy group and $R_d$ denotes an —A—B group wherein A denotes a —OCH$_2$CH$_2$ group, where the alkylene moiety is linked to the group B, and B denotes a piperazino group wherein a hydrogen atom in the 3 position together with the hydrogen atom in the 4 position is replaced by a —CH$_2$—O—CO—CH$_2$— bridge, while the left-hand end of the abovementioned bridge is bound to the 3 position of the piperazino ring, a piperazino group which is substituted in the 4 position by a 2-oxo-tetrahydrofuran-3-yl, 2-oxo-tetrahydrofuran-4-yl-, 2-oxo-tetrahydrofuranylmethyl or 2-oxo-tetrahydrofuranylcarbonyl group, the tautomers, stereoisomers and the salts thereof.

The following are mentioned as examples of particularly preferred compounds:

(1) 4-[(3-chloro-4-fluorophenyl) amino]-6-cyclopentylmethoxy-7-{2-[4-(2-oxo-tetrahydrofuran-4-yl)-piperazin-1-yl]-ethoxy}-quinazoline, (2) 4-[(3-chloro-4-fluorophenyl)amino]-6-cyclopentyloxy-7-{2-[4-(2-oxo-tetrahydrofuran-4-yl)-piperazin-1-yl]-ethoxy}-quinazoline, (3) 4-[(3-chloro-4-fluorophenyl)amino]-6-cyclopropylmethoxy-7-{2-[4-(2-oxo-tetrahydrofuran-4-yl)-piperazin-1-yl]-ethoxy}-quinazoline and (4) 4-[(3-chloro-4-fluorophenyl)amino]-6-cyclopropylmethoxy-7-(2-{4-[(R)-(2-oxo-tetrahydrofuran-5-yl)methyl]-piperazin-1-yl}-ethoxy)-quinazoline, the tautomers, stereoisomers and the salts thereof.

The compounds of general formula I may be prepared by the following methods, for example:

a) reacting a compound of general formula

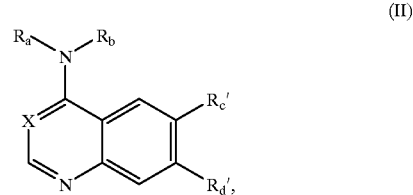

(II)

optionally formed in the reaction mixture wherein $R_a$, $R_b$ and X are as hereinbefore defined, one of the groups $R_c'$ or $R_d'$ denotes a —C—D group as mentioned hereinbefore for $R_c$ or $R_d$ and the other group $R_c'$ or $R_d'$ denotes an —A'—Z$_1$ group, where A' denotes a C$_{1-6}$-alkylene or —O—C$_{1-6}$-alkylene group and Z$_1$ denotes an exchangeable group such as a halogen atom or a substituted sulphinyl or sulphonyl group, e.g. a chlorine or bromine atom, a methylsulphinyl, propylsulphinyl, phenylsulphinyl, benzylsulphinyl, methylsulphonyl, propylsulphonyl, phenylsulphonyl or benzylsulphonyl group, with a compound of general formula:

H—G ,(III)

wherein

G represents one of the groups mentioned for B hereinbefore, which is linked to the group A via a nitrogen atom.

The reaction is expediently carried out in a solvent such as acetonitrile, tetrahydrofuran, dioxan, toluene, chlorobenzene, dimethylformamide, dimethylsulphoxide, methylene chloride, ethylene glycol diethyl ether or sulpholane, optionally in the presence of an inorganic or tertiary organic base, e.g. sodium carbonate or potassium hydroxide, a tertiary organic base such as triethylamine or N-ethyl-diisopropylamine (Hünig base), whilst these organic bases may simultaneously also serve as solvent, and optionally in the presence of a reaction accelerator such as an alkali metal iodide at temperatures between −20 and 150° C., but preferably at temperatures between −10 and 100° C. The reaction may, however, also be carried out without a solvent or in an excess of the compound of general formula III used.

b. In order to prepare a compound of general formula I wherein one of the groups $R_c$ or $R_d$ represents a —A—B' group where A is as hereinbefore defined and B' represents one of the groups mentioned for B hereinbefore which contains an imino or $HNR_4$ group substituted by $R_6$ or by an $R_5$—$C_{1-4}$-alkyl group, where $R_4$ to $R_6$ are as hereinbefore defined: reacting a compound of general formula:

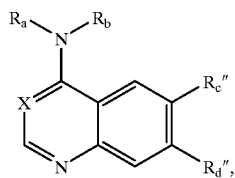

(IV)

wherein $R_a$, $R_b$ and X are as hereinbefore defined, one of the groups $R_c''$ or $R_d''$ denotes a —C—D group mentioned above for $R_c$ or $R_d$ and the other group $R_c''$ or $R_d''$ denotes an —A—B" group, where A, C and D are as hereinbefore defined and B" represents a group which can be converted by alkylation into a group B', where B' represents one of the groups mentioned for B hereinbefore which contains an imino or $HNR_4$ group substituted by $R_6$ or by an $R_5$—$C_{1-4}$-alkyl group, where $R_a$ to $R_a$ are as hereinbefore defined, with a compound of general formula:

 $Z_2$—U         ,(V)

wherein

U denotes the group $R_6$ or a $R_5$—$C_{1-4}$-alkyl group, where $R_5$ and $R_6$ are as hereinbefore defined, and $Z_2$ denotes an exchangeable group such as a halogen atom or a substituted sulphonyloxy group, e.g. a chlorine or bromine atom, a methylsulphonyloxy, propylsulphonyloxy, phenylsulphonyloxy or benzylsulphonyloxy group, or $Z_2$ together with an adjacent hydrogen atom denotes another carbon-carbon bond which is linked to a carbonyl group.

The reaction is expediently carried out in a solvent such as methanol, ethanol, isopropanol, acetonitrile or dimethylformamide and optionally in the presence of a base such as tri-ethylamine, N-ethyl-diisopropylamine or potassium carbonate at temperatures between 0 and 150° C., but preferably at temperatures between 20 and 100° C.

If in a compound of general formula V $Z_2$ denotes an exchangeable group, the reaction is preferably carried out in a solvent or mixture of solvents such as acetonitrile, methylene chloride, dimethylformamide, dimethyl sulphoxide, sulpholane, benzene, toluene, chlorobenzene, tetrahydrofuran, benzene/tetrahydrofuran or dioxan, expediently in the presence of a tertiary organic base such as triethylamine or N-ethyl-diisopropylamine (Hünig base), while these organic bases may simultaneously also serve as solvent, or in the presence of an inorganic base such as sodium carbonate, potassium carbonate or sodium hydroxide solution, expediently at temperatures between −20 and 200° C., preferably at temperatures between 0 and 150° C., or if in a compound of general formula V $Z_2$ together with an adjacent hydrogen atom denotes another carbon-carbon bond which is linked to a carbonyl group, the reaction is preferably carried out in a solvent such as methanol, ethanol, isopropanol or acetonitrile at temperatures between 0 and 100° C., but preferably between 20° C. and the boiling temperature of the reaction mixture.

c. In order to prepare a compound of general formula I wherein one of the groups $R_c$ or $R_d$ denotes an —A—B' group, where A is as hereinbefore defined and B' represents one of the groups mentioned for B hereinbefore which contains an imino or $HNR_4$ group substituted by an $R_5CO$, $R_5$—$C_{1-4}$-alkylene-CO, $(R_4NR_6)$—$C_{1-4}$-alkylene-CO, $R_6O$—$C_{1-4}$-alkylene-CO, $R_6S$—$C_{1-4}$-alkylene-CO, $R_6SO$—$C_{1-4}$-alkylene-CO, $R_6SO_2$—$C_{1-4}$-alkylene-CO or 2-oxo-morpholino -$C_{1-4}$-alkylene-CO group, where $R_4$ to $R_6$ are as hereinbefore defined and the 2-oxo-morpholino moiety may be substituted by one or two $C_{1-2}$-alkyl groups:

reacting a compound of general formula:

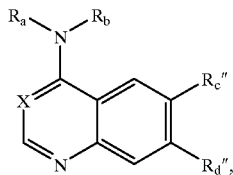

(IV)

wherein $R_a$, $R_b$ and X are as hereinbefore defined, one of the groups $R_c''$ or $R_d''$ denotes a —C—D group mentioned for $R_c$ or $R_d$ hereinbefore and the other group $R_c''$ or $R_d''$ denotes an —A—B" group, where A, C and D are as hereinbefore defined and B" represents a group which can be converted by acylation into a group B', where B' represents one of the groups mentioned for B hereinbefore which contains an imino or $HNR_4$ group substituted by an $R_5CO$, $R_5$—$C_{1-4}$-alkylene-CO, $(R_4NR_6)$—$C_{1-4}$-alkylene-CO, $R_6O$—$C_{1-4}$-alkylene-CO, $R_6S$—$C_{1-4}$-alkylene-CO, $R_6SO$—$C_{1-4}$-alkylene-CO, $R_6SO_2$—$C_{1-4}$-alkylene-CO or 2-oxo-morpholino-$C_{1-4}$-alkylene-CO group, where $R_4$ to $R_6$ are as hereinbefore defined and the 2-oxo-morpholino moiety may be substituted by one or two $C_{1-2}$-alkyl groups, with a compound of general formula:

 HO—CO—W         ,(VI)

wherein

W represents the group $R_5$ or an $R_5$—$C_{1-4}$-alkyl, $(R_4NR_6)$—$C_{1-4}$-alkyl, $R_6O$—$C_{1-4}$-alkyl, $R_6S$—$C_{1-4}$-alkyl, $R_6SO$—$C_{1-4}$-alkyl, $R_6SO_2$—$C_{1-4}$-alkyl or 2-oxo-morpholino-$C_{1-4}$-alkyl group, wherein $R_4$ to $R_6$ are as hereinbefore defined and the 2-oxo-morpholino moiety may be substituted by one or two $C_{1-2}$-alkyl groups.

The reaction is optionally carried out in a solvent or mixture of solvents such as methylene chloride, dimethylformamide, benzene, toluene, chlorobenzene, tetrahydrofuran or dioxan, optionally in the presence of a dehydrating agent, e.g. in the presence of isobutyl chloroformate, thionyl chloride, trimethylchlorosilane, phosphorus trichloride, phosphorus pentoxide, N,N'-dicyclohexylcarbodiimide, N,N'-dicyclohexyl-carbodiimide/N-hydroxysuccinimide, N,N'-carbonyldiimidazole, triphenyl-phosphine/carbon tetrachloride or O-(benzotriazol-1-yl)-N,N,N',N'-tetramethyluronium-tetrafluoroborate or with a corresponding reactive derivative such as a corresponding ester, acid halide or anhydride, optionally with the addition of an inorganic or organic base, preferably with the addition of an organic base such as triethylamine, N-ethyl-diisopropylamine or 4-dimethylamino-pyridine, expediently at temperatures between 0 and 150° C., preferably at temperatures between 0 and 80° C.

In the reactions described hereinbefore, any reactive groups present such as hydroxy, carboxy, amino, alkylamino or imino groups may be protected during the reaction by conventional protecting groups which are cleaved again after the reaction.

For example, a protecting group for a hydroxy group may be a trimethylsilyl, acetyl, benzoyl, methyl, ethyl, tert.butyl, trityl, benzyl or tetrahydropyranyl group, protecting groups for a carboxy group may be a trimethylsilyl, methyl, ethyl, tert.butyl, benzyl or tetrahydropyranyl group, and protecting groups for an amino, alkylamino or imino group may be a formyl, acetyl, trifluoroacetyl, ethoxycarbonyl, tert.butoxycarbonyl, benzyloxycarbonyl, benzyl, methoxy-benzyl or 2,4-dimethoxybenzyl group, and additionally phthalyl, for the amino group.

Any protecting group used is optionally subsequently cleaved for example by hydrolysis in an aqueous solvent, e.g. in water, isopropanol/water, acetic acid/water, tetrahydrofuran/water or dioxan/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane optionally using a solvent such as methylene chloride, dioxan, methanol or diethyl ether.

A trifluoroacetyl group is preferably cleaved by treating with an acid such as hydrochloric acid, optionally in the presence of a solvent such as acetic acid at temperatures between 50 and 120° C. or by treating with sodium hydroxide solution, optionally in the presence of a solvent such as tetrahydrofuran at temperatures between 0 and 50° C.

A phthalyl group is preferably cleaved in the presence of hydrazine or a primary amine such as methylamine, ethylamine or n-butylamine in a solvent such as methanol, ethanol, isopropanol, toluene/water or dioxan, at temperatures between 20 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

The compounds of general formulae II to VI used as starting materials are known from the literature in some cases or may be obtained by methods known from the literature (cf. Examples I to XIV).

As already mentioned hereinbefore, the compounds of general formula I according to the invention and the physiologically acceptable salts thereof have valuable pharmacological properties, particularly an inhibiting effect on signal transduction mediated by the Epidermal Growth Factor receptor (EGF-R), whilst this may be achieved for example by inhibiting ligand bonding, receptor dimerisation or tyrosine kinase itself. It is also possible that the transmission of signals to components located further down is blocked.

The biological properties of the new compounds were investigated as follows:

The inhibition of the EGF-R-mediated signal transmission can be demonstrated e.g. with cells which express human EGF-R and whose survival and proliferation depend on stimulation by EGF or TGF-alpha. A cell line of murine origin dependent on interleukin-3-(IL-3) which was genetically modified to express functional human EGF-R was used here. The proliferation of these cells known as F/L-HERc can therefore be stimulated either by murine IL-3 or by EGF (cf. von Rüden, T. et al. in EMBO J. 7, 2749–2756 (1988). and Pierce, J. H. et al. in Science 239, 628–631 (1988)).

The starting material used for the F/L-HERc cells was the cell line FDC-$P_1$, the production of which has been described by Dexter, T. M. et al. in J. Exp. Med. 152, 1036–1047 (1980). Alternatively, however, other growth-factor-dependent cells may also be used (cf. for example Pierce, J. H. et al. in Science 239, 628–631 (1988), Shibuya, H. et al. in Cell 70, 57–67 (1992) and Alexander, W. S. et al. in EMBO J. 10, 3683–3691 (1991)). For expressing the human EGF-R cDNA (cf. Ullrich, A. et al. in Nature 309, 418–425 (1984)) recombinant retroviruses were used as described by von Rüden, T. et al., EMBO J. 7, 2749–2756 (1988), except that the retroviral vector LXSN (cf. Miller, A. D. et al. in BioTechniques 7, 980–990 (1989)) was used for the expression of the EGF-R cDNA and the line GP+E86 (cf. Markowitz, D. et al. in J. Virol. 62, 1120–1124 (1988)) was used as the packaging cell.

The test was performed as follows:

F/L-HERc cells were cultivated in RPMI/1640 medium (Bio Whittaker), supplemented with 10% foetal calf serum (FCS, Boehringer Mannheim), 2 mM glutamine (Bio Whittaker), standard antibiotics and 20 ng/ml of human EGF (Promega), at 37° C. and 5% $CO_2$. In order to investigate the inhibitory activity of the compounds according to the invention, $1.5 \times 10^4$ cells per well were cultivated in triplicate in 96-well dishes in the above medium (200 μl), the cell proliferation being stimulated with either EGF (20 ng/ml) or murine IL-3. The IL-3 used was obtained from culture supernatants of the cell line X63/0 mIL-3 (cf. Karasuyama, H. et al. in Eur. J. Immunol. 18, 97–104 (1988)). The compounds according to the invention were dissolved in 100% dimethylsulphoxide (DMSO) and added to the cultures in various dilutions, the maximum DMSO concentration being 1%. The cultures were incubated for 48 hours at 37° C.

In order to determine the inhibitory activity of the compounds according to the invention the relative cell number was measured in O.D. units using the Cell Titer 96™ AQueous Non-Radioactive Cell Proliferation Assay (Promega). The relative cell number was calculated as a percentage of the control (F/LHERc cells without inhibitor) and the concentration of active substance which inhibits the proliferation of the cells by 50% ($IC_{50}$) was derived therefrom. The following results were obtained:

| compound (Example No.) | Inhibition of the EGF-dependent proliferation $IC_{50}$ [nM] |
|---|---|
| 1 | 4 |
| 3 | 62 |
| 3(1) | 11 |
| 4 | 67 |

The compounds of general formula I according to the invention thus inhibit signal transduction by tyrosine kinases, as demonstrated by the example of the human EGF receptor, and are therefore useful for treating pathophysiological processes caused by hyperfunction of tyrosine kinases. These are e.g. benign or malignant tumours, particularly tumours of epithelial and neuroepithelial origin, metastasisation and the abnormal proliferation of vascular endothelial cells (neoangiogenesis).

The compounds according to the invention are also useful for preventing and treating diseases of the airways and lungs which are accompanied by increased or altered production of mucus caused by stimulation by tyrosine kinases, e.g. in inflammatory diseases of the airways such as chronic bronchitis, chronic obstructive bronchitis, asthma, bronchiectasis, allergic or non-allergic rhinitis or sinusitis, cystic fibrosis, α1-antitrypsin deficiency, or coughs, pulmonary emphysema, pulmonary fibrosis and hyperreactive airways.

The compounds are also suitable for treating diseases of the gastrointestinal tract and bile duct and gall bladder which are associated with disrupted activity of the tyrosine kinases, such as may be found e.g. in chronic inflammatory changes such as cholecystitis, Crohn's disease, ulcerative colitis, and ulcers in the gastrointestinal tract or such as may occur in diseases of the gastrointestinal tract which are associated with increased secretions, such as Ménétrier's disease, secreting adenomas and protein loss syndrome, and also for treating nasal polyps and polyps of the gastrointestinal tract of various origins such as villous or adenomatous polyps of the large intestine, but also polyps in familial polyposis coli, in intestinal polyps in Gardner's syndrome, in polyps throughout the entire gastro-intestinal tract in Peutz-Jeghers Syndrome, in inflammatory pseudopolyps, in juvenile polyps, in colitis cystica profunda and in pneumatosis cystoides intestinales.

In addition, the compounds of general formula I and the physiologically acceptable salts thereof may be used to treat kidney diseases, particularly in cystic changes as in cystic kidneys, for treating renal cysts which may be idiopathic in origin or occur in syndromes such as tubercular sclerosis, in von Hippel-Lindau syndrome, in nephrophthisis and spongy kidney and other diseases caused by abnormal function of tyrosine kinases, such as e.g. epidermal hyperproliferation (psoriasis), inflammatory processes, diseases of the immune system, hyperproliferation of haematopoietic cells, etc.

By reason of their biological properties the compounds according to the invention may be used on their own or in conjunction with other pharmacologically active compounds, for example in tumour therapy, in monotherapy or in conjunction with other anti-tumour therapeutic agents, for example in combination with topoisomerase inhibitors (e.g. etoposide), mitosis inhibitors (e.g. vinblastine), compounds which interact with nucleic acids (e.g. cis-platin, cyclophosphamide, adriamycin), hormone antagonists (e.g. tamoxifen), inhibitors of metabolic processes (e.g. 5-FU etc.), cytokines (e.g. interferons), antibodies, etc. For treating respiratory tract diseases, these compounds may be used on their own or in conjunction with other therapeutic agents for the airways, such as substances with a secretolytic, broncholytic and/or anti-inflammatory activity. For treating diseases in the region of the gastrointestinal tract, these compounds may also be administered on their own or in conjunction with substances having an effect on motility or secretion, or anti-inflammatory substances. These combinations may be administered either simultaneously or sequentially.

These compounds may be administered either on their own or in conjunction with other active substances by intravenous, subcutaneous, intramuscular, intraperitoneal or intranasal route, by inhalation or transdermally or orally, whilst aerosol formulations are particularly suitable for inhalation.

For pharmaceutical use the compounds according to the invention are generally used for warm-blooded vertebrates, particularly humans, in doses of 0.01–100 mg/kg of body weight, preferably 0.1–15 mg/kg. For administration they are formulated with one or more conventional inert carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof in conventional galenic preparations such as plain or coated tablets, capsules, powders, suspensions, solutions, sprays or suppositories.

The following Examples are intended to illustrate the present invention without restricting it:

Preparation of the Starting Compounds:

EXAMPLE I

4-[(3-chloro-4-fluorophenyl)amino]-6-cyclopentyloxy-7-[2-(piperazin-1-yl)-ethoxy]-quinazoline 2.00 ml trifluoroacetic acid are added dropwise to 740 mg of 4-[(3-chloro-4-fluorophenyl)amino]-6-cyclopentyloxy-7-

{2-[4-(tert.butyloxycarbonyl)-piperazin-1-yl]-ethoxy}-quinazoline in 10 ml of methylene chloride. The reaction solution is stirred overnight at ambient temperature. For working up the reaction mixture is concentrated by evaporation, combined with 20 ml of water and made alkaline with concentrated aqueous ammonia solution. The aqueous phase is extracted with ethyl acetate. The combined extracts are washed with saturated sodium carbonate solution and saturated sodium chloride solution, dried over magnesium sulphate and concentrated by evaporation. A light yellow solid remains.

Yield: 570 mg (93% of theory), Melting point: 134–137, 5° C. Mass spectrum (ESI⁻): m/z 484, 486 [M–H]⁻

The following compounds are obtained analogously to Example I:

(1) 4-[(3-chloro-4-fluorophenyl)amino]-6-cyclopentylmethoxy-7-[2-(piperazin-1-yl)-ethoxy]-quinazoline $R_f$ value: 0.05 (silica gel, methylene chloride/methanol/concentrated aqueous ammonia solution=90:10:0.1) Mass spectrum (ESI⁻): m/z=498, 500 [M–H]⁻

(2) Perhydro-pyrazino[2,1-c][1,4]oxazin-3-one x 2 trifluoroacetic acid (The reaction mixture is concentrated by evaporation without aqueous working up)

Mass spectrum (ESI⁺): m/z=157 [M+H]⁺

(3) 4-[(3-chloro-4-fluorophenyl)amino]-6-cyclopropylmethoxy-7-[2-(piperazin-1-yl)-ethoxy]-quinazoline $R_f$ value: 0.10 (silica gel, methylene chloride/methanol/concentrated aqueous ammonia solution=90:10:1) Mass spectrum (ESI⁺): m/z=472, 474 [M+H]⁺

(4) 2-Oxo-3-[(piperidin-4-yl)sulfanyl]-tetrahydrofuran x trifluoroacetic acid (the reaction mixture is concentrated by evaporation without aqueous working up)

$R_f$ value: 0.66 (Reversed Phase ready-made TLC plate (E. Merck), acetonitrile/water/trifluoroacetic acid=50:50:1) Mass spectrum (ESI⁺): m/z=202 [M+H]⁺

EXAMPLE II

4-[(3-chloro-4-fluorophenyl)amino]-6-cyclopentyloxy-7-{2-[4-(tert.butyloxycarbonyl)-piperazin-1-yl]-ethoxy}-quinazoline 340 mg of 1,8-diazabicyclo[5.4.0]undec-7-ene are added at ambient temperature to 940 mg of 4-[(3-chloro-4-fluorophenyl)amino]-6-cyclopentyloxy-7-(2-bromoethoxy)-quinazoline and 1.00 g of N-(tert.butyloxycarbonyl)-piperazine in 30 ml of acetonitrile. The reaction mixture is heated to 60° C. for five hours. Then a further 0.2 g of N-(tert.butyloxycarbonyl)-piperazine and some 1,8-diazabicyclo[5.4.0]undec-7-ene are added. The yellow reaction solution is stirred for two hours at 60° C. and then overnight at ambient temperature, during which time a white precipitate is formed. This is suction filtered, washed with a little acetonitrile and dried. 453 mg of the desired product are obtained as a white solid. The mother liquor is concentrated by evaporation and the flask residue is chromatographed over a silica gel column with methylene chloride/methanol (95:5). Another 300 mg of the desired product are obtained.

Yield: 753 mg (66% of theory), $R_f$ value: 0.53 (silica gel, methylene chloride/methanol/concentrated aqueous ammonia solution=90:10:0.1) Mass spectrum (ESI⁻): m/z=584, 586 [M–H]⁻

The following compounds are obtained analogously to Example II:

(1) 4-[(3-chloro-4-fluorophenyl)amino]-6-cyclopentylmethoxy-7-{2-[4-(tert.butyloxycarbonyl)-piperazin-1-yl]-ethoxy}-quinazoline (The reaction is carried out in the presence of potassium carbonate, diisopropylethylamine and benzyl-tributyl-ammonium chloride in dioxan/water (20:1))

$R_f$ value: 0.55 (silica gel, methylene chloride/methanol/concentrated aqueous ammonia solution=90:10:0.1) Mass spectrum (ESI⁻): m/z=598, 600 [M–H]⁻

(2) 4-[(3-chloro-4-fluorophenyl)amino]-6-cyclopropylmethoxy-7-{2-[4-(tert.butyloxycarbonyl)-piperazin-1-yl]-quinazoline $R_f$ value: 0.43 (silica gel, methylene chloride/methanol/concentrated aqueous ammonia solution=90:10:0.1) Mass spectrum (ESI⁻): m/z=570, 572 [M–H]⁻

(3) 4-[(3-chloro-4-fluoro-phenyl)amino]-6-[2-(4-{N-[(tert.-butyloxycarbonyl)methyl]-N-(2-hydroxy-ethyl)-amino}-piperidin-1-yl)-ethoxy]-7-methoxy-quinazoline (The reaction is carried out in the presence of diisopropylethylamine as an auxiliary base.)

$R_f$ value: 0.22 (silica gel, ethyl acetate/methanol/concentrated aqueous ammonia solution=90:10:0.5) Mass spectrum (ESI⁻): m/z=602, 604 [M–H]⁻

(4) 4-[(3-chloro-4-fluoro-phenyl)amino]-6-[2-(4-{N-[(tert.-butyloxycarbonyl)methyl]-N-(2-hydroxy-ethyl)-amino}-piperidin-1-yl)-ethoxy]-7-((R)-tetrahydrofuran-3-yloxy)-quinazoline (The reaction is carried out in the presence of diisopropylethylamine as an auxiliary base.)

$R_f$ value: 0.24 (silica gel, ethyl acetate/methanol/concentrated aqueous ammonia solution=90:10:0.5) Mass spectrum (ESI⁺): m/z=660, 662 [M+H]⁺

EXAMPLE III

4-[(3-chloro-4-fluorophenyl)amino]-6-cyclopentylmethoxy-7-(2-bromoethoxy)-quinazoline 4.84 g of potassium carbonate are added to 3.50 g of 4-[(3-chloro-4-fluorophenyl)amino]-6-cyclopentylmethoxy-7-hydroxy-quinazoline and 6.89 ml of 1,2-dibromoethane in 40 ml of N,N-dimethylformamide. The reaction mixture is stirred under a nitrogen atmosphere for 1.5 hours at 80° C. After cooling to ambient temperature the reaction mixture is filtered and the filtrate is evaporated down in vacuo. The oily, brown residue is cooled in an ice bath and triturated with a little methanol, whereupon a yellowish solid crystallises out. The precipitate is suction filtered, washed with cold methanol and dried in the vacuum desiccator.

Yield: 2.60 g (58% of theory), $R_f$ value: 0.82 (silica gel, methylene chloride/methanol 9:1) Mass spectrum (ESI⁺): m/z=494, 496, 498 [M+H]⁺

The following compounds are obtained analogously to Example III:

(1) (2) 4-[(3-chloro-4-fluorophenyl)amino]-6-cyclopentyloxy-7-(2-bromoethoxy)-quinazoline $R_f$ value: 0.65 (silica gel, methylene chloride/methanol/concentrated aqueous ammonia solution=90:10:0.1) Mass spectrum (ESI⁻): m/z=478, 480, 482 [M–H]⁻

(2) 4-[(3-chloro-4-fluorophenyl)amino]-6-cyclopropylmethoxy-7-(2-bromoethoxy)-quinazoline
(The reaction is carried out in acetonitrile)

$R_f$ value: 0.72 (silica gel, methylene chloride/methanol/concentrated aqueous ammonia solution=90:10:0.1)
Mass spectrum (ESI⁻): m/z=464, 466, 468 [M–H]⁻

(3) 4-[(3-chloro-4-fluoro-phenyl)amino]-6-(2-bromo-ethoxy)-7-((R)-tetrahydrofuran-3-yloxy)-quinazoline (The reaction is carried out in acetonitrile at 60° C.)

$R_f$ value: 0.37 (silica gel, methylene chloride/methanol=9:1)
Mass spectrum (ESI⁻): m/z=480, 482, 484 [M–H]⁻

EXAMPLE IV

4-[(3-chloro-4-fluorophenyl)amino]-6-cyclopentylmethoxy-7-hydroxy-quinazoline 4.99 g of 4-[(3-chloro-4-fluorophenyl)amino]-6-cyclopentylmethoxy-7-methylcarbonyloxy-quinazoline are suspended in 80 ml methanol and combined with 1.80 ml of concentrated aqueous ammonia solution. The reaction mixture is stirred overnight at ambient temperature. For working up the reaction mixture is diluted with 500 ml methylene chloride, washed with water and saturated sodium chloride solution, dried over magnesium sulphate and concentrated by evaporation. 4.30 g of a brownish solid are obtained. The crude product is stirred with tert.butylmethylether, suction filtered, washed with a little tert.butylmethylether and dried in vacuo at ambient temperature.

Yield: 3.59 g (80% of theory), $R_f$ value: 0.48 (silica gel, methylene chloride/methanol/concentrated aqueous ammonia solution=90:10:0.1) Mass spectrum (ESI⁺): m/z=388, 340 [M+H]⁺

The following compounds are obtained analogously to Example IV:

(1) 4-[(3-chloro-4-fluorophenyl)amino]-6-cyclopentyloxy-7-hydroxy-quinazoline $R_f$ value: 0.53 (silica gel, methylene chloride/methanol/concentrated aqueous ammonia solution=90:10:0.1) Mass spectrum (ESI⁺): m/z=374, 376 [M+H]⁺

(2) 4-[(3-chloro-4-fluorophenyl)amino]-6-cyclopropylmethoxy-7-hydroxy-quinazoline $R_f$ value: 0.56 (silica gel, methylene chloride/methanol=9:1) Mass spectrum (ESI⁻): m/z=358, 360 [M–H]⁻

EXAMPLE V

4-[(3-chloro-4-fluorophenyl)amino]-6-cyclopentylmethoxy-7-methylcarbonyloxy-quinazoline 4.03 g of 4-chloro-6-cyclopentylmethoxy-7-methylcarbonyloxy-quinazoline are suspended in 70 ml of isopropanol and combined with 1.95 g of 3-chloro-4-fluoro-aniline. The reaction mixture is refluxed for two hours under a nitrogen atmosphere. After cooling to ambient temperature the light-coloured precipitate formed is suction filtered, washed with a little isopropanol and dried in the air.

Yield: 4.99 g (92% of theory), $R_f$ value: 0.80 (silica gel, methylene chloride/methanol/concentrated aqueous ammonia solution=90:10:0.1) Mass spectrum (ESI⁺): m/z=430, 432 [M+H]⁺

The following compounds are obtained analogously to Example V:

(1) 4-[(3-chloro-4-fluorophenyl)amino]-6-cyclopentyloxy-7-methylcarbonyloxy-quinazoline $R_f$ value: 0.73 (silica gel, methylene chloride/methanol/concentrated aqueous ammonia solution=90:10:0.1) Mass spectrum (ESI⁺): m/z=416, 418 [M+H]⁺

(2) 4-[(3-chloro-4-fluorophenyl)amino]-6-cyclopropylmethoxy-7-methylcarbonyloxy-quinazoline $R_f$ value: 0.86 (silica gel, methylene chloride/methanol=9:1) Mass spectrum (ESI⁺): m/z=402, 404 [M+H]⁺

EXAMPLE VI 4-chloro-6-cyclopentylmethoxy-7-methylcarbonyloxy-quinazoline 3.80 g of 4-hydroxy-6-cyclopentylmethoxy-7-methylcarbonyloxy-quinazoline are suspended in 90 ml thionyl chloride and heated to boiling in a nitrogen atmosphere. After the addition of four drops of N,N-dimethylformamide the reaction mixture is refluxed for a further two hours. After cooling to ambient temperature the excess thionyl chloride is distilled off in a water jet vacuum. The brown residue is stirred with 30 ml of toluene. The solvent is distilled off and 4.30 g of a greyish-brown solid remain, which is reacted further without any more purification.

$R_f$ value: 0.89 (silica gel, methylene chloride/methanol/concentrated aqueous ammonia solution=90:10:0.1)

The following compounds are obtained analogously to Example VI:

(1) 4-chloro-6-cyclopentyloxy-7-methylcarbonyloxy-quinazoline $R_f$ value: 0.69 (silica gel, methylene chloride/methanol/concentrated aqueous ammonia solution=90:10:0.1)

(2) 4-chloro-6-cyclopropylmethoxy-7-methylcarbonyloxy-quinazoline $R_f$ value: 0.84 (silica gel, methylene chloride/methanol=9:1)

EXAMPLE VII 4-hydroxy-6-cyclopentylmethoxy-7-methylcarbonyloxy-quinazoline 4.30 g of 4,7-dihydroxy-6-cyclopentylmethoxy-quinazoline in 100 ml of pyridine are heated to 80° C. under a nitrogen atmosphere. 1.80 ml of acetic anhydride are added to the dark-brown suspension. The reaction mixture is stirred for three hours at 80° C., during which time a total solution is formed. After cooling to ambient temperature the reaction mixture is poured onto about 800 ml of ice water. The precipitate formed is suction filtered and washed thoroughly with water. The light grey solid is dried in the vacuum desiccator.

Yield: 3.82 g (77% of theory), $R_f$ value: 0.49 (silica gel, methylene chloride/methanol=9:1) Mass spectrum (ESI$^-$): m/z=301 [M−H]$^-$ The following compounds are obtained analogously to Example VII:

(1) 4-hydroxy-6-cyclopentyloxy-7-methylcarbonyloxy-quinazoline

Melting point: 209–212° C. Mass spectrum (ESI$^-$): m/z=287 [M−H]$^-$ (2) 4-hydroxy-6-cyclopropylmethoxy-7-methylcarbonyloxy-quinazoline $R_f$ value: 0.53 (silica gel, methylene chloride/methanol=9:1) Mass spectrum (ESI$^-$): m/z=273 [M−H]$^-$

EXAMPLE VIII 4,7-Dihydroxy-6-cyclopentylmethoxy-quinazoline 5.76 g of 2-amino-5-cyclopentylmethoxy-4-hydroxy-benzoic acid and 6.52 g of formamidine acetate in 140 ml ethanol are refluxed for about three hours. For working up the reaction mixture is evaporated down to about 100 ml and combined with 300 ml of ice water, whereupon a grey precipitate is formed. The precipitate is suction filtered, washed with water and dried in the vacuum desiccator.

Yield: 4.57 g (77% of theory), $R_f$ value: 0.25 (silica gel, methylene chloride/methanol=95:5) Mass spectrum (ESI$^-$): m/z=259 [M−H]$^-$ The following compounds are obtained analogously to Example VIII:

(1) 4,7-Dihydroxy-6-cyclopentyloxy-quinazoline $R_f$ value: 0.42 (silica gel, methylene chloride/methanol/concentrated aqueous ammonia solution=90:10:0.1) Mass spectrum (ESI$^+$): m/z=246 [M+H]$^+$ (2) 4,7-Dihydroxy-6-cyclopropylmethoxy-quinazoline $R_f$ value: 0.45 (silica gel, methylene chloride/methanol concentrated aqueous ammonia solution=90:10:0.1) Mass spectrum (ESI$^-$): m/z=231 [M−H]$^-$

EXAMPLE IX 2-amino-5-cyclopentylmethoxy-4-hydroxy-benzoic acid 6.50 g of 5-cyclopentylmethoxy-4-hydroxy-2-nitro-benzoic acid are dissolved in 130 ml methanol, combined with 2.00 g of Raney-Nickel and hydrogenated under a hydrogen pressure of 50 psi for about three hours at ambient temperature until the calculated amount of hydrogen has been taken up. The catalyst is filtered off and washed with hot methanol. The filtrate is evaporated down in vacuo. A brownish solid remains, which is reacted further without any more purification.

Yield: 5.79 g (100% of theory), $R_f$ value: 0.67 (silica gel, methylene chloride/methanol=9:1) Mass spectrum (ESI$^-$): m/z=250 [M−H]$^-$ The following compounds are obtained analogously to Example IX:

(1) 2-amino-5-cyclopentyloxy-4-hydroxy-benzoic acid $R_f$ value: 0.38 (silica gel, methylene chloride/methanol/concentrated aqueous ammonia solution=90:10:0.1) Mass spectrum (ESI$^+$): m/z=238 [M+H]$^+$ (2) 2-amino-5-cyclopropylmethoxy-4-hydroxy-benzoic acid $R_f$ value: 0.51 (silica gel, methylene chloride/methanol/concentrated aqueous ammonia solution=90:10:0.1) Mass spectrum (ESI$^-$): m/z=222 [M−H]$^-$

EXAMPLE X 5-cyclopentylmethoxy-4-hydroxy-2-nitro-benzoic acid 15.37 g of 4,5-methylendioxy-2-nitro-benzoic acid and 51.84 ml of cyclopentylmethanol are dissolved in 100 ml of dimethyl sulphoxide and cooled in an ice bath under a nitrogen atmosphere. Then 3.90 g of sodium are added in batches. The reaction mixture is stirred for 30 minutes while cooling with an ice bath, then briefly heated to 35–40° C. and subsequently stirred for a further three hours while cooling with an ice bath. Then the ice bath is removed and the reaction mixture is stirred overnight at ambient temperature. The reddish-dark brown reaction solution is poured onto about 800 ml of acetone, whereupon a dark brown precipitate is formed. The precipitate is suction filtered, washed with acetone, dissolved in 300–400 ml water and adjusted to about pH 2 with 60 ml of 2N hydrochloric acid. The aqueous solution is extracted several times with methylene chloride. The combined extracts are washed with saturated sodium chloride solution, dried over sodium sulphate and concentrated by evaporation. The dark-brown oily flask residue is dissolved in 800 ml of methylene chloride and purified through a silica gel charge with methylene chloride/methanol (9:1). A brown oil is obtained which is crystallised by stirring with water while cooling with an ice bath. The brownish precipitate formed is suction filtered, washed with a little water and dried in the vacuum desiccator.

Yield: 9.55 g (47% of theory), $R_f$ value: 0.67 (silica gel, toluene/dioxan/ethanol/glacial acetic acid=90:10:10:6) Mass spectrum (ESI$^-$): m/z=280 [M−H]$^-$ The following compounds are obtained analogously to Example X:

(1) 5-cyclopentyloxy-4-hydroxy-2-nitro-benzoic acid $R_f$ value: 0.62 (silica gel, toluene/dioxan/ethanol/glacial acetic acid=90:10:10:6) Mass spectrum (ESI$^-$): m/z=266 [M−H]$^-$ (2) 5-cyclopropylmethoxy-4-hydroxy-2-nitro-benzoic acid $R_f$ value: 0.61 (silica gel, toluene/dioxan/ethanol/glacial acetic acid=90:10:10:6) Mass spectrum (ESI$^-$): m/z=252 [M−H]$^-$

EXAMPLE XI 8-(tert.butyloxycarbonyl)-perhydro-pyrazino[2,1-c][1,4]oxazin-3-one 2.00 g of 1-(tert.butyloxycarbonyl)-4-[(ethoxycarbonyl)methyl]-3-hydroxymethyl-piperazine in 2.5 ml of acetonitrile are combined with 500 mg of p-toluenesulphonic acid-monohydrate. The reaction mixture is refluxed for three hours until the reaction is finished. Then the solvent is distilled off in vacuo. The crude product is further reacted directly without any more purification.

$R_f$ value: 0.80 (silica gel, ethyl acetate/methanol=9:1)

EXAMPLE XII 1-(tert.butyloxycarbonyl)-4-[(ethoxycarbonyl) methyl]-3-hydroxymethyl-piperazine and 8-(tert.butyloxycarbonyl)-perhydro-pyrazino[2,1-c][1,4]oxazin-3-one 3.90 ml of ethyl bromoacetate are added to 5.80 g of 1-(tert.butyloxycarbonyl)-3-hydroxymethyl-piperazine and 4.50 ml of triethylamine in 60 ml of acetonitrile. The reaction mixture is refluxed overnight, during which time, according to thin layer chromatography, two products are formed. For working up the reaction mixture is evaporated down in vacuo and the residue is divided between ethyl acetate and water. The organic phase is dried over magnesium sulphate, concentrated by evaporation and chromatographed over a silica gel column with ethyl acetate/methanol (97:3). The following two products are obtained as yellowish oils: 8-(tert.butyloxycarbonyl)-perhydro-pyrazino[2,1-c][1,4]oxazin-3-one Yield: 3.43 g (50% of theory), $R_f$ value: 0.80 (silica gel, ethyl acetate/methanol=9:1)

1-(tert.butyloxycarbonyl)-4-[(ethoxycarbonyl) methyl]-3-hydroxymethyl-piperazine Yield: 2.08 g (26% of theory), $R_f$ value: 0.58 (silica gel, ethyl acetate/methanol=9:1) Mass spectrum (ESI$^+$): m/z=303 [M+H]$^+$

EXAMPLE XIII 1-(tert.butyloxycarbonyl)-3-hydroxymethyl-piperazine

A solution of 8.00 g of 1-(tert.butyloxycarbonyl)-3-ethoxycarbonyl-piperazine in 10 ml of tetrahydrofuran is added dropwise to a suspension of 900 mg of lithium borohydride in 20 ml of tetrahydrofuran and then the resulting mixture is refluxed for three hours. For working up the reaction mixture is concentrated by evaporation, adjusted to pH 4 with 10% aqueous citric acid solution and stirred for about 40 minutes while cooling with an ice bath. Then the mixture is made alkaline with concentrated sodium hydroxide solution and left to stand overnight. The next morning, it is extracted with tert.butylmethylether. The organic phase is dried over magnesium sulphate and concentrated by evaporation. A clear oil is left, which slowly crystallises.

Yield: 5.80 g (87% of theory), $R_f$ value: 0.28 (silica gel, ethyl acetate/methanol=4:1) Mass spectrum (ESI$^+$): m/z=217 [M+H]$^+$

EXAMPLE XIV 1-(tert.butyloxycarbonyl)-3-ethoxycarbonyl-piperazine 21.80 g of di-tert.butyl pyrocarbonate are added to 15.80 g of 2-ethoxycarbonyl-piperazine in 400 ml ethanol while cooling with an ice bath. The reaction mixture is stirred for another three hours at 0° C. Then it is concentrated by evaporation and the residue is divided between ethyl acetate and water. The organic phase is dried over magnesium sulphate, concentrated by evaporation and purified by chromatography over a silica gel column with ethyl acetate/methanol (95:5) as eluant.

Yield: 24.30 g (94% of theory), $R_f$ value: 0.40 (silica gel, ethyl acetate/methanol=9:1) Mass spectrum (ESI$^+$): m/z=281 [M+Na]$^+$

EXAMPLE XV

4-{N-[(tert.-Butyloxycarbonyl)methyl]-N-(2-hydroxy-ethyl)-amino}-piperidine

The compound is obtained by hydrogenation of 1-benzyloxycarbonyl-4-{N-[(tert.-butyloxycarbonyl) methyl]-N-(2-hydroxy-ethyl)-amino}-piperidine in ethanol in the presence of 10% palladium on activated carbon in a Parr Apparatus.

Mass spectrum (ESI$^+$): m/z=259 [M+H]$^+$

EXAMPLE XVI

1-Benzyloxycarbonyl-4-{N-[(tert.-butyloxycarbonyl) methyl]-N-(2-hydroxy-ethyl)-amino}-piperidine 1.2 ml of acetic acid are added to 4.89 g 1-benzyloxycarbonyl-4-oxo-piperidine and 3.67 g tert.-butyl (2-hydroxy-ethylamino)-acetate in 100 ml methylene chloride and cooled in an ice-water bath. Then a total of 4.44 g sodium triacetoxyborohydride are added in batches over a period of one hour. The reaction mixture is allowed to warm up overnight. For working up the mixture is added to saturated sodium hydrogen carbonate solution. The organic phase is separated, dried over magnesium sulfate and concentrated by evaporation. The crude product is purified chromatographically on a silica gel column with ethyl acetate/pet. ether (1:1) as eluant.

Yield: 3.52 g (43% of theory) $R_f$ value: 0.40 (silica gel, cyclohexane/ethyl acetate=1:1) Mass spectrum (ESI$^+$): m/z=393 [M+H]$^+$

EXAMPLE XVII

4-[(3-chloro-4-fluoro-phenyl)amino]-6-hydroxy-7-((R)-tetrahydrofuran-3-yloxy)-quinazoline The compound is obtained by treatment of 4-[(3-chloro-4-fluoro-phenyl)amino]-6-benzyloxy-7-((R)-tetrahydrofuran-3-yloxy)-quinazoline with trifluoroacetic acid under reflux.

$R_f$ value: 0.32 (silica gel, methylene chloride/methanol=9:1)

EXAMPLE XVIII

4-[(3-chloro-4-fluoro-phenyl)amino]-6-benzyloxy-7-((R)-tetrahydrofuran-3-yloxy) quinazoline 5.03 ml Diethyl azodicarboxylate are added dropwise to a solution of 8.00 g 4-[(3-chloro-4-fluoro-phenyl)amino]-6-benzyloxy-7-hydroxy-quinazoline (see WO 0055141 A1) and 2.42 ml (S)-(+)-3-hydroxy-tetrahydrofuran and 7.95 g triphenylphosphine in 160 ml tetrahydrofuran. The reaction mixture is stirred overnight at room temperature and subsequently concentrated by evaporation in the rotary evaporator. The flask residue is purified chromatographically on a silica gel column with methylene chloride/ethyl acetate (gradient from 2:1 to 1:2) as eluant.

Yield: 7.34 g (78% of theory) Melting point: 165–168° C. Mass spectrum (ESI$^+$): m/z 466,468 [M+H]$^+$

EXAMPLE XIX

2-Oxo-3-{[1-(tert.-butyloxycarbonyl)-piperidin-4-yl]sulfanyl}-tetrahydrofuran

The compound is obtained by reaction of 1-(tert.-butyloxycarbonyl)-4-mercapto-piperidine with 3-bromo-dihydro-furan-2-one in N,N-dimethylformamide in the presence of potassium tert.butylate.

$R_f$ value: 0.35 (silica gel, cyclohexane/ethyl acetate=3:2) Mass spectrum (ESI$^-$): m/z=300 [M–H]$^-$ Preparation of the final compounds:

EXAMPLE 1

4-[(3-chloro-4-fluorophenyl)amino]-6-cyclopentyloxy-7-{2-[4-(2-oxo-tetrahydrofuran-3-yl)-piperazin-1-yl]-ethoxy}-quinazoline 67 mg of 3-bromo-dihydrofuran-2-one are added to 180 mg of 4-[(3-chloro-4-fluorophenyl)amino]-6-cyclopentyloxy-7-[2-(piperazin-1-yl)-ethoxy]-quinazoline and 0.14 ml of triethylamine in 4 ml of tetrahydrofuran. The reaction mixture is stirred at ambient temperature over the weekend. For working up the reaction mixture is evaporated down in vacuo using the rotary evaporator. The residue is chromatographed over a silica gel column with methylene chloride/methanol (95:5 to 90:10). The light-coloured solid thus obtained is stirred with diethylether, suction filtered and dried in a drying gun in vacuo at 60° C.

Yield: 120 mg (% of theory), $R_f$ value: 0.38 (silica gel, methylene chloride/methanol/concentrated aqueous ammonia solution=90:10:0.1) Mass spectrum (ESI$^-$): m/z=568, 570 [M–H]$^-$

EXAMPLE 2

4-[(3-chloro-4-fluorophenyl)amino]-6-cyclopentylmethoxy-7-(2-{4-[(S)-(2-oxo-tetrahydrofuran-5-yl)carbonyl]-piperazin-1-yl}-ethoxy)-quinazoline 72 mg of (S)-(+)-5-oxo-tetrahydrofuran-2-carboxylic acid are dissolved in 2.5 ml of N,N-dimethylformamide, combined with 183 mg of (benzotriazol-1-yl)-N,N,N',N'-tetramethyl-uronium-tetrafluoroborate and stirred for 30 minutes at ambient temperature. This solution is then added to a mixture of 250 mg of 4-[(3-chloro-4-fluorophenyl)amino]-6-cyclopentylmethoxy-7-[2-(piperazin-1-yl)-ethoxy]-quinazoline and 110 μl of triethylamine in 2.5 ml of N,N-dimethylformamide. The reaction mixture is stirred for five hours at ambient temperature. For working up the mixture is poured onto 50 ml of water. A white precipitate is formed, which is suction filtered and washed with water. The crude product is purified by chromatography over an Alox column (activity stage III) with methylene chloride/methanol (98:2) as eluant. The desired product is obtained as a light-coloured solid.

Yield: 78 mg (26% of theory), $R_f$ value: 0.46 (silica gel, methylene chloride/methanol/concentrated aqueous ammonia solution=90:10:0.1) Mass spectrum (ESI$^-$): m/z=610, 612 [M–H]$^-$ The following compound is obtained analogously to Example 2:

(1) 4-[(3-chloro-4-fluorophenyl)amino]-6-cyclopentyloxy-7-(2-{4-[(S)-(2-oxo-tetrahydrofuran-5-yl)carbonyl]-piperazin-1-yl}-ethoxy)-quinazoline $R_f$ value: 0.37 (silica gel, methylene chloride/methanol/concentrated aqueous ammonia solution=90:10:0.1) Mass spectrum (ESI$^-$): m/z=596, 598 [M–H]$^-$

EXAMPLE 3

4-[(3-chloro-4-fluorophenyl)amino]-6-cyclopentylmethoxy-7-{2-[4-(2-oxo-tetrahydrofuran-4-yl)-piperazin-1-yl]-ethoxy}-quinazoline 46 mg of (5H)-furan-2-one are added to a solution of 230 mg of 4-[(3-chloro-4-fluorophenyl)amino]-6-cyclopentylmethoxy-7-[2-(piperazin-1-yl)-ethoxy]-quinazoline in 2 ml of methanol. The reaction mixture is stirred for 24 hours at ambient temperature, then for another six at 50° C. In total, six more drops of (5H)-furan-2-one are added until the reaction is complete. The solvent is distilled off using the rotary evaporator and the crude product is purified by chromatography over an Alox column (activity stage III) with methylene chloride/methanol (98:2) as eluant. The desired product is obtained as a colourless solid.

Yield: 106 mg (40% of theory), $R_f$ value: 0.50 (silica gel, methylene chloride/methanol/concentrated aqueous ammonia solution=90:10:0.1) Mass spectrum (ESI$^-$): m/z=582, 584 [M–H]$^-$ The following compounds are obtained analogously to Example 3:

(1) 4-[(3-chloro-4-fluorophenyl)amino]-6-cyclopentyloxy-7-{2-[4-(2-oxo-tetrahydrofuran-4-yl)-piperazin-1-yl]-ethoxy}-quinazoline $R_f$ value: 0.42 (silica gel, methylene chloride/methanol/concentrated aqueous ammonia solution=90:10:1) Mass spectrum (ESI$^-$): m/z=468, 470 [M–H]$^-$ (2) 4-[(3-chloro-4-fluorophenyl)amino]-6-cyclopropylmethoxy-7-{2-[4-(2-oxo-tetrahydrofuran-4-yl)-piperazin-1-yl]-ethoxy}-quinazoline $R_f$ value: 0.35 (silica gel, methylene chloride/methanol/concentrated aqueous ammonia solution=90:10:1) Mass spectrum (ESI$^-$): m/z=554, 556 [M–H]$^-$

EXAMPLE 4

4-[(3-chloro-4-fluorophenyl)amino]-6-cyclopentyloxy-7-(2-{4-[(R)-(2-oxo-tetrahydrofuran-5-yl)methyl]-piperazin-1-yl}-ethoxy)-quinazoline 160 mg of potassium carbonate and 50 mg of sodium iodide are added to 300 mg of 4-[(3-chloro-4-fluorophenyl)amino]-6-cyclopentyloxy-7-[2-(piperazin-1-yl)-ethoxy]-quinazoline in 20 ml of acetonitrile. Then 170 mg of (R)-5-[(methanesulphonyl-oxy)methyl]-2-oxo-tetrahydrofuran are added. The reaction mixture is refluxed for four hours, then a further 0.10 g of (R)-5-[(methanesulphonyloxy)methyl]-2-oxo-tetrahydrofuran are added. After another ten hours of refluxing a further 0.12 g of (R)-5-[(methanesulphonyloxy)methyl]-2-oxo-tetrahydrofuran as well as 0.20 g of potassium carbonate and 70 mg of sodium iodide are added. The reaction mixture is refluxed for another five hours and then left to stand over a weekend. For working up the reaction mixture is filtered and the filtrate is concentrated by evaporation. The crude product is purified by chromatography over a silica gel column with methylene chloride/methanol/concentrated aqueous ammonia solution (95:5:0.05, later 93:7:0.1) as eluant. The title compound is obtained as a white solid.

Yield: 170 mg (47% of theory), $R_f$ value: 0.35 (silica gel, methylene chloride/methanol/concentrated aqueous ammonia solution=90:10:1) Mass spectrum (ESI$^-$): m/z=582, 584 [M–H]$^-$ The following compounds are obtained analogously to Example 4:

(1) 4-[(3-chloro-4-fluorophenyl)amino]-6-cyclopentylmethoxy-7-(2-{4-[(R)-(2-oxo-tetrahydrofuran-5-yl)methyl]-piperazin-1-yl}-ethoxy)-quinazoline $R_f$ value: 0.50 (silica gel, methylene chloride/methanol/concentrated aqueous ammonia solution=90:10:0.1) Mass spectrum (ESI⁻): m/z=596, 598 [M–H]⁻

(2) 4-[(3-chloro-4-fluorophenyl)amino]-6-cyclopropylmethoxy-7-(2-{4-[(R)-(2-oxo-tetrahydrofuran-5-yl)methyl]-piperazin-1-yl}-ethoxy)-quinazoline $R_f$ value: 0.36 (silica gel, methylene chloride/methanol/concentrated aqueous ammonia solution=90:10:1) Mass spectrum (ESI⁻): m/z=568, 570 [M–H]⁻

EXAMPLE 5

4-[(3-chloro-4-fluorophenyl)amino]-6-cyclopropylmethoxy-7-[2-(3-oxo-perhydro-pyrazino[2,1-c][1,4]oxazin-8-yl)-ethoxy]-quinazoline 0.25 ml of diisopropylethylamine and 260 mg of perhydro-pyrazino[2,1-c][1,4]oxazin-3-one x 2 trifluoroacetic acid are added to 150 mg of 4-[(3-chloro-4-fluorophenyl)amino]-6-cyclopropylmethoxy-7-(2-bromoethoxy)-quinazoline in 15 ml of acetonitrile. The reaction mixture is stirred for one hour at ambient temperature and then refluxed for two hours. Then 70 mg of potassium carbonate and 75 mg of sodium iodide are added. The reaction mixture is refluxed for about another 14 hours, during which time a total of another 175 mg of perhydro-pyrazino[2,1-c][1,4]oxazin-3-one x 2 trifluoroacetic acid and 300 mg of potassium carbonate are added successively until the reaction is complete. For working up the inorganic salts are filtered off and the filtrate is evaporated down in vacuo. The flask residue is chromatographed over a silica gel column with methylene chloride/methanol (95:5) as eluant. The desired product is obtained as a light brown resin. Yield: 27 mg (16% of theory), $R_f$ value: 0.50 (silica gel, methylene chloride/methanol/concentrated aqueous ammonia solution=90:10:0.1) Mass spectrum (EI): m/z=541, 543 [M]⁺

The following compounds are obtained analogously to Example 5:

(1) 4-[(3-chloro-4-fluoro-phenyl)amino]-6-(2-{4-[(2-oxo-tetrahydrofuran-3-yl)sulfanyl]-piperidin-1-yl}-ethoxy)-7-methoxy-quinazoline $R_f$ value: 0.42 (silica gel, ethyl acetate/methanol/concentrated aqueous ammonia solution=90:10:0.5) Mass spectrum (EI): m/z=546, 548 [M]⁺

EXAMPLE 6

4-[(3-chloro-4-fluoro-phenyl)amino]-6-{2-[4-(2-oxo-morpholin-4-yl)-piperidin-1-yl]-ethoxy}-7-methoxy-quinazoline The compound is obtained by treatment of 4-[(3-chloro-4-fluoro-phenyl)amino]-6-[2-(4-{N-[(tert.-butyloxycarbonyl)-methyl]-N-(2-hydroxy-ethyl)-amino}-piperidin-1-yl)-ethoxy]-7-methoxy-quinazoline with trifluoroacetic acid in acetonitrile under reflux.

$R_f$ value: 0.10 (silica gel, ethyl acetate/methanol/concentrated aqueous ammonia solution=90:10:0.5) Mass spectrum (ESI⁻): m/z=528, 530 [M–H]⁻

The following compounds are obtained analogously to Example 6:

(1) 4-[(3-chloro-4-fluoro-phenyl)amino]-6-{2-[4-(2-oxo-morpholin-4-yl)-piperidin-1-yl]-ethoxy}-7-((R)-tetrahydrofuran-3-yloxy)-quinazoline $R_f$ value: 0.11 (silica gel, ethyl acetate/methanol/concentrated aqueous ammonia solution=90:10:0.5) Mass spectrum (ESI⁻): m/z=584, 586 [M–H]⁻

The following compounds are obtained analogously to the preceding Examples:

(1) 4-[(3-chloro-4-fluorophenyl)amino]-7-methoxy-6-{3-[4-(2-oxo-tetrahydrofuran-4-yl)-piperazin-1-yl]-propyloxy}-quinazoline (2) 4-[(3-chloro-4-fluorophenyl)amino]-7-methoxy-6-(3-{4-[(2-oxo-tetrahydrofuran-5-yl)methyl]-piperazin-1-yl}-propyloxy)-quinazoline (3) 4-[(3-chloro-4-fluorophenyl)amino]-7-methoxy-6-(3-{4-[(2-oxo-tetrahydrofuran-5-yl)carbonyl]-piperazin-1-yl}-propyloxy)-quinazoline (4) 4-[(3-chloro-4-fluorophenyl)amino]-7-methoxy-6-(3-{4-{2-[(2-oxo-tetrahydrofuran-3-yl)sulphanyl]-ethyl}-piperazin-1-yl}-propyloxy)-quinazoline (5) 4-[(3-chloro-4-fluorophenyl)amino]-7-methoxy-6-{3-[1-(2-oxo-tetrahydrofuran-4-yl)-piperidin-4-yl]-propyloxy}-quinazoline (6) 4-[(3-chloro-4-fluorophenyl)amino]-7-methoxy-6-[3-(3-oxo-perhydro-pyrazino[2,1-c][1,4]oxazin-8-yl)-propyloxy]-quinazoline (7) 4-[(3-chloro-4-fluorophenyl)amino]-7-methoxy-6-[3-(1-oxo-perhydro-pyrazino[2,1-c][1,4]oxazin-8-yl)-propyloxy]-quinazoline (8) 4-[(3-chloro-4-fluorophenyl)amino]-7-methoxy-6-[3-(2-oxa-3-oxo-8-aza-spiro[4.5]dec-8-yl)-propyloxy]-quinazoline (9) 4-[(3-chloro-4-fluorophenyl)amino]-7-methoxy-6-[3-(3-oxa-2-oxo-9-aza-spiro[5.5]undecan-9-yl)-propyloxy]-quinazoline

(10) 4-[(3-chloro-4-fluorophenyl)amino]-7-cyclopropylmethoxy-6-[3-(3-oxa-2-oxo-9-aza-spiro[5.5]undecan-9-yl)-propyloxy]-quinazoline

(11) 4-[(3-chloro-4-fluorophenyl)amino]-7-methoxy-6-[2-(3-oxa-2-oxo-9-aza-spiro[5.5]undecan-9-yl)-ethoxy]-quinazoline

(12) 4-[(R)-(1-phenyl-ethyl)amino]-7-methoxy-6-[2-(3-oxa-2-oxo-9-aza-spiro[5.5]undecan-9-yl)-ethoxy]-quinazoline

(13) 4-[(3-chloro-4-fluorophenyl)amino]-7-methoxy-6-[3-(1,4-dioxa-2-oxo-9-aza-spiro[5.5]undecan-9-yl)-propyloxy]-quinazoline

(14) 4-[(3-chloro-4-fluorophenyl)amino]-7-methoxy-6-[3-(4-methyl-1-oxa-2-oxo-4,9-diaza-spiro[5.5]undecan-9-yl)-propyloxy]-quinazoline

(15) 4-[(3-chloro-4-fluorophenyl)amino]-7-cyclopropylmethoxy-6-[3-(4-methyl-1-oxa-2-oxo-4,9-diaza-spiro[5.5]undecan-9-yl)-propyloxy]-quinazoline

(16) 4-[(3-chloro-4-fluorophenyl)amino]-7-cyclopropylmethoxy-6-[2-(4-methyl-1-oxa-2-oxo-4,9-diaza-spiro[5.5]undecan-9-yl)-ethoxy]-quinazoline

(17) 4-[(3-chloro-4-fluorophenyl)amino]-7-methoxy-6-{3-[4-(2-oxo-molpholin-4-yl)-piperidin-1-yl]-propyloxy}-quinazoline

(18) 4-[(3-chloro-4-fluorophenyl)amino]-7-methoxy-6-{2-[4-(2-oxo-morpholin-4-yl)-piperidin-1-yl]-ethoxy}-quinazoline

(19) 4-[(3-chloro-4-fluorophenyl)amino]-7-methoxy-6-{3-[4-(6-methyl-2-oxo-morpholin-4-yl)-piperidin-1-yl]-propyloxy}-quinazoline
(20) 4-[(3-chloro-4-fluorophenyl)amino]-7-cyclopropylmethoxy-6-{3-[4-(6-methyl-2-oxo-morpholin-4-yl)-piperidin-1-yl]-propyloxy}-quinazoline
(21) 4-[(3-chloro-4-fluorophenyl)amino]-7-methoxy-6-(3-{4-[(6-methyl-2-oxo-morpholin-4-yl)methyl]-piperidin-1-yl}-propyloxy)-quinazoline
(22) 4-[(3-chloro-4-fluorophenyl)amino]-7-methoxy-6-(3-{4-[(2-oxo-tetrahydrofuran-3-yl)sulphanyl]-piperidin-1-yl}-propyloxy)-quinazoline
(23) 4-[(3-chloro-4-fluorophenyl)amino]-7-methoxy-6-[3-(6-methoxymethyl-2-oxo-morpholin-4-yl)-propyloxy]-quinazoline
(24) 4-[(3-chloro-4-fluorophenyl)amino]-7-methoxy-6-{3-[6-(2-methoxy-ethyl)-2-oxo-morpholin-4-yl]-propyloxy}-quinazoline
(25) 4-[(3-chloro-4-fluorophenyl)amino]-7-methoxy-6-[3-(1,9-dioxa-2-oxo-4-aza-spiro[5.5]undecan-4-yl)-propyloxy]-quinazoline
(26) 4-[(3-chloro-4-fluorophenyl)amino]-6-methoxy-7-{-3-[4-(2-oxo-tetrahydrofuran-4-yl)-piperazin-1-yl]-propyloxy}-quinazoline
(27) 4-[(3-chloro-4-fluorophenyl)amino]-6-methoxy-7-(3-{4-[(2-oxo-tetrahydrofuran-5-yl)methyl]-piperazin-1-yl}-propyloxy)-quinazoline
(28) 4-[(3-chloro-4-fluorophenyl)amino]-6-methoxy-7-(3-{4-[(2-oxo-tetrahydrofuran-5-yl)carbonyl]-piperazin-1-yl}-propyloxy)-quinazoline
(29) 4-[(3-chloro-4-fluorophenyl)amino]-6-methoxy-7-(3-{4-{2-[(2-oxo-tetrahydrofuran-3-yl)sulphanyl]-ethyl}-piperazin-1-yl}-propyloxy)-quinazoline
(30) 4-[(3-chloro-4-fluorophenyl)amino]-6-methoxy-7-{3-[1-(2-oxo-tetrahydrofuran-4-yl)-piperidin-4-yl]-propyloxy}-quinazoline
(31) 4-[(3-chloro-4-fluorophenyl)amino]-6-methoxy-7-[3-(3-oxo-perhydro-pyrazino[2,1-c][1,4]oxazin-8-yl)-propyloxy]-quinazoline
(32) 4-[(3-chloro-4-fluorophenyl)amino]-6-methoxy-7-[3-(1-oxo-perhydro-pyrazino[2,1-c][1,4]oxazin-8-yl)-propyloxy]-quinazoline
(33) 4-[(3-chloro-4-fluorophenyl)amino]-6-methoxy-7-[3-(2-oxa-3-oxo-8-aza-spiro[4.5]dec-8-yl)-propyloxy]-quinazoline
(34) 4-[(3-chloro-4-fluorophenyl)amino]-6-methoxy-7-[3-(3-oxa-2-oxo-9-aza-spiro[5.5]undecan-9-yl)-propyloxy]-quinazoline
(35) 4-[(3-chloro-4-fluorophenyl)amino]-6-cyclopropylmethoxy-7-[3-(3-oxa-2-oxo-9-aza-spiro[5.5]undecan-9-yl)-propyloxy]-quinazoline
(36) 4-[(3-chloro-4-fluorophenyl)amino]-6-methoxy-7-[2-(3-oxa-2-oxo-9-aza-spiro[5.5]undecan-9-yl)-ethoxy]-quinazoline
(37) 4-[(R)-(1-phenyl-ethyl)amino]-6-methoxy-7-[2-(3-oxa-2-oxo-9-aza-spiro[5.5]undecan-9-yl)-ethoxy]-quinazoline
(38) 4-[(3-chloro-4-fluorophenyl)amino]-6-methoxy-7-[3-(1,4-dioxa-2-oxo-9-aza-spiro[5.5]undecan-9-yl)-propyloxy]-quinazoline
(39) 4-[(3-chloro-4-fluorophenyl)amino]-6-methoxy-7-[3-(4-methyl-1-oxa-2-oxo-4,9-diaza-spiro[5.5]undecan-9-yl)-propyloxy]-quinazoline
(40) 4-[(3-chloro-4-fluorophenyl)amino]-6-cyclopropylmethoxy-7-[3-(4-methyl-1-oxa-2-oxo-4,9-diaza-spiro[5.5]undecan-9-yl)-propyloxy]-quinazoline
(41) 4-[(3-chloro-4-fluorophenyl)amino]-6-cyclopropylmethoxy-7-[2-(4-methyl-1-oxa-2-oxo-4,9-diaza-spiro[5.5]undecan-9-yl)-ethoxy]-quinazoline
(42) 4-[(3-chloro-4-fluorophenyl)amino]-6-methoxy-7-{3-[4-(2-oxo-morpholin-4-yl)-piperidin-1-yl]-propyloxy}-quinazoline
(43) 4-[(3-chloro-4-fluorophenyl)amino]-6-methoxy-7-{2-[4-(2-oxo-morpholin-4-yl)-piperidin-1-yl]-ethoxy}-quinazoline
(44) 4-[(3-chloro-4-fluorophenyl)amino]-6-methoxy-7-{3-[4-(6-methyl-2-oxo-morpholin-4-yl)-piperidin-1-yl]-propyloxy}-quinazoline
(45) 4-[(3-chloro-4-fluorophenyl)amino]-6-cyclopropylmethoxy-7-{3-[4-(6-methyl-2-oxo-morpholin-4-yl)-piperidin-1-yl]-propyloxy}-quinazoline
(46) 4-[(3-chloro-4-fluorophenyl)amino]-6-methoxy-7-(3-{4-[(6-methyl-2-oxo-morpholin-4-yl)methyl]-piperidin-1-yl}-propyloxy)-quinazoline
(47) 4-[(3-chloro-4-fluorophenyl)amino]-6-methoxy-7-(3-{4-[(2-oxo-tetrahydrofuran-3-yl)sulphanyl]-piperidin-1-yl}-propyloxy)-quinazoline
(48) 4-[(3-chloro-4-fluorophenyl)amino]-6-methoxy-7-[3-(6-methoxymethyl-2-oxo-morpholin-4-yl)-propyloxy]-quinazoline
(49) 4-[(3-chloro-4-fluorophenyl)amino]-6-methoxy-7-{3-[6-(2-methoxy-ethyl)-2-oxo-morpholin-4-yl]-propyloxy}-quinazoline
(50) 4-[(3-chloro-4-fluorophenyl)amino]-6-methoxy-7-[3-(1,9-dioxa-2-oxo-4-aza-spiro[5.5]undecan-4-yl)-propyloxy]-quinazoline
(51) 4-[(3-chloro-4-fluorophenyl)amino]-7-(tetrahydrofuran-3-yloxy)-6-{2-[4-(2-oxo-morpholin-4-yl)-piperidin-1-yl]-ethoxy}-quinazoline
(52) 4-[(3-chloro-4-fluorophenyl)amino]-7-(tetrahydropyran-4-yloxy)-6-{4-[4-(2-oxo-morpholin-4-yl)-piperidin-1-yl]-butyloxy}-quinazoline
(53) 4-[(3-chloro-4-fluorophenyl)amino]-7-(tetrahydrofuran-2-ylmethoxy)-6-{2-[4-(2-oxo-morpholin-4-yl)-piperidin-1-yl]-ethoxy}-quinazoline
(54) 4-[(3-chloro-4-fluorophenyl)amino]-7-(tetrahydropyran-4-ylmethoxy)-6-{2-[4-(2-oxo-morpholin-4-yl)-piperidin-1-yl]-ethoxy}-quinazoline
(55) 4-[(3-chloro-4-fluorophenyl)amino]-6-(tetrahydrofuran-3-yloxy)-7-{2-[4-(2-oxo-morpholin-4-yl)-piperidin-1-yl]-ethoxy}-quinazoline
(56) 4-[(3-chloro-4-fluorophenyl)amino]-6-(tetrahydropyran-4-yloxy)-7-{4-[4-(2-oxo-morpholin-4-yl)-piperidin-1-yl]-butyloxy}-quinazoline
(57) 4-[(3-chloro-4-fluorophenyl)amino]-6-(tetrahydrofuran-2-ylmethoxy)-7-{2-[4-(2-oxo-morpholin-4-yl)-piperidin-1-yl]-ethoxy}-quinazoline
(58) 4-[(3-chloro-4-fluorophenyl)amino]-6-(tetrahydropyran-4-ylmethoxy)-7-{2-[4-(2-oxo-morpholin-4-yl)-piperidin-1-yl]-ethoxy}-quinazoline

EXAMPLE 7

Coated tablets containing 75 mg of active substance

| 1 tablet core contains: | |
| --- | --- |
| active substance | 75.0 mg |
| calcium phosphate | 93.0 mg |
| corn starch | 35.5 mg |

-continued

| 1 tablet core contains: | |
|---|---|
| polyvinylpyrrolidone | 10.0 mg |
| hydroxypropylmethylcellulose | 15.0 mg |
| magnesium stearate | 1.5 mg |
| | 230.0 mg |

Preparation

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

| Weight of core: | 230 mg |
|---|---|
| Die: | 9 mm, convex |

The tablet cores thus produced are coated with a film consisting essentially of hydroxypropylmethylcellulose. The finished film-coated tablets are polished with beeswax.

| Weight of coated tablet: | 245 mg. |
|---|---|

EXAMPLE 8

Tablets containing 100 mg of active substance

Composition

| 1 tablet contains: | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

| Weight of tablet: | 220 mg |
|---|---|
| Diameter: | 10 mm, biplanar, facetted on both sides and notched on one side. |

EXAMPLE 9

Tablets containing 150 mg of active substance

Composition

| 1 tablet contains: | |
|---|---|
| active substance | 50.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| Weight of tablet: | 300 mg |
|---|---|
| die: | 10 mm, flat |

EXAMPLE 10

Hard gelatine capsules containing 150 mg of active substance

| 1 capsule contains: | |
|---|---|
| active substance | 50.0 mg |
| corn starch (dried) approx. | 80.0 mg |
| lactose (powdered) approx. | 87.0 mg |
| magnesium stearate | 3.0 mg |
| approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

| Capsule filling: | approx. 320 mg |
|---|---|
| Capsule shell: | size 1 hard gelatine capsule. |

EXAMPLE 11

Suppositories containing 150 mg of active substance

| 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation

After the suppository mass has been melted the active substance is homogeneously distributed therein and the melt is poured into chilled moulds.

EXAMPLE 12

Suspension containing 50 mg of active substance

| 100 ml of suspension contain: | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water ad | 100 ml |

Preparation

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 13

Ampoules containing 10 mg active substance

| Composition: | |
|---|---|
| active substance | 10.0 mg |
| 0.01 N hydrochloric acid q.s. | |
| double-distilled water ad | 2.0 ml |

Preparation

The active substance is dissolved in the necessary amount of 0.01 N HCl, made isotonic with common salt, filtered sterile and transferred into 2 ml ampoules.

EXAMPLE 14

Ampoules containing 50 mg of active substance

| Composition: | |
|---|---|
| active substance | 50.0 mg |
| 0.01 N hydrochloric acid q.s. | |
| double-distilled water ad | 10.0 ml |

Preparation

The active substance is dissolved in the necessary amount of 0.01 N HCl, made isotonic with common salt, filtered sterile and transferred into 10 ml ampoules.

EXAMPLE 15

Capsules for powder inhalation containing 5 mg of active substance

| 1 capsule contains: | |
|---|---|
| active substance | 5.0 mg |
| lactose for inhalation | 15.0 mg |
| | 20.0 mg |

Preparation

The active substance is mixed with lactose for inhalation. The mixture is packed into capsules in a capsule-making machine (weight of the empty capsule approx. 50 mg).

| weight of capsule: | 70.0 mg |
|---|---|
| size of capsule = | 3 |

EXAMPLE 16

Solution for inhalation for hand-held nebulisers containing 2.5 mg active substance

| 1 spray contains: | |
|---|---|
| active substance | 2.500 mg |
| benzalkonium chloride | 0.001 mg |
| 1N hydrochloric acid q.s. | |
| ethanol/water (50/50) ad | 15.000 mg |

Preparation

The active substance and benzalkonium chloride are dissolved in ethanol/water (50/50). The pH of the solution is adjusted with 1N hydrochloric acid. The resulting solution is filtered and transferred into suitable containers for use in hand-held nebulisers (cartridges).

Contents of the container: 4.5 g

What is claimed is:

1. A compound of the formula:

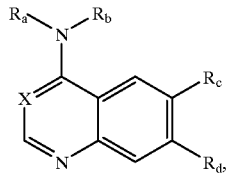

(I)

wherein

X denotes a nitrogen atom, $R_a$ denotes a hydrogen atom or a methyl group, $R_b$ denotes a phenyl, benzyl or 1-phenylethyl group, wherein the phenyl nucleus in each case is substituted by the groups $R_1$ to $R_3$, where $R_1$ and $R_2$, which may be identical or different, each denote a hydrogen, fluorine, chlorine, bromine or iodine atom, a methyl, ethyl, hydroxy, methoxy, ethoxy, amino, cyano, vinyl or ethynyl group, an aryl, aryloxy, arylmethyl or arylmethoxy group, a methyl or methoxy group substituted by 1 to 3 fluorine atoms or $R_1$ together with $R_2$, if they are bound to adjacent carbon atoms, denotes a —CH=CH—CH=CH, —CH=CH—NH or —CH=N—NH group and $R^3$ denotes a hydrogen, fluorine, chlorine or bromine atom, one of the groups $R_c$ or $R_d$ denotes an —A—B group and the other group $R_c$ or $R_d$ denotes a —C—D group, where A denotes a $C_{1-6}$-alkylene group, a —O—$C_{1-6}$-alkylene group, where the alkylene moiety is linked to the group B, or an oxygen atom, with the proviso that if A is an oxygen atom it may not be linked to the group B via a nitrogen atom of the group B, and B denotes a pyrrolidino group wherein the two hydrogen atoms in the 2 position are replaced by a group E, wherein E represents a —CH$_2$—O—CO—CH$_2$, —CH$_2$CH$_2$—O—CO, —CH$_2$—O—CO—CH$_2$CH$_2$, —CH$_2$CH$_2$—O—CO—CH$_2$ or —CH$_2$CH$_2$CH$_2$—O—CO— bridge optionally substituted by one or two $C_{1-2}$-alkyl groups, a pyrrolidino group wherein the two hydrogen atoms in the 3 position are replaced by a group F wherein F denotes an —O—CO—CH$_2$CH$_2$, —CH$_2$—O—CO—CH$_2$, —CH$_2$CH$_2$—O—CO, —O—CO—CH$_2$CH$_2$CH$_2$, —CH$_2$—O—CO—CH$_2$CH$_2$, —CH$_2$CH$_2$—O—CO—CH$_2$, —CH$_2$CH$_2$CH$_2$—O—CO, —O—CO—CH$_2$—NR$_4$—CH$_2$, —CH$_2$—O—CO—CH$_2$—NR$_4$, —O—CO—CH$_2$—O—CH$_2$ or —CH$_2$—O—CO—CH$_2$—O— bridge optionally substituted by one or two $C_{1-2}$-alkyl groups, where $R_4$ denotes a hydrogen atom or a $C_{1-4}$-alkyl group, a piperidino or hexahydroazepino group, wherein the two hydrogen atoms in the 2 position are replaced by a group E, where E is as hereinbefore defined, a piperidino or hexahydroazepino group, wherein in each case the two hydrogen atoms in the 3 position or in the 4 position are replaced by a group F, where F is as hereinbefore defined, a piperazino or 4-($C_{1-4}$-alkyl)-piperazino group, wherein the two hydrogen atoms in the 2 position or in the 3 position of the piperazino ring are replaced by a group E, where E is as hereinbefore defined, a pyrrolidino or piperidino group, wherein two neighbouring hydrogen atoms are replaced by a —O—CO—CH$_2$, —CH$_2$—O—CO, —O—CO—CH$_2$CH$_2$, —CH$_2$—O—CO—CH$_2$, —CH$_2$CH$_2$—O—CO, —O—CO—CH$_2$—NR$_4$ or —O—CO—CH$_2$—O— bridge optionally substituted by one or two $C_{1-2}$-alkyl groups, where $R_4$ is as hereinbefore defined and the heteroatoms of the abovementioned bridges are not bound to the 2 or 5 position of the pyrrolidino ring and are not bound to the 2 or 6 position of the piperidino ring, a piperazino or 4-($C_{1-4}$-alkyl)-piperazino group, wherein a hydrogen atom in the 2 position together with a hydrogen atom in the 3 position of the piperazino ring are replaced by a —CH$_2$—O—CO—CH$_2$ or —CH$_2$CH$_2$—O—CO— bridge optionally substituted by one or two $C_{1-2}$-alkyl groups, a piperazino group wherein a hydrogen atom in the 3 position together with the hydrogen atom in the 4 position are replaced by a —CO—O—CH$_2$CH$_2$ or —CH$_2$—O—CO—CH$_2$— bridge optionally substituted by one or two $C_{1-2}$-alkyl groups, where in each case the left-hand end of the abovementioned bridges is bound to the 3 position of the piperazino ring, a pyrrolidino, piperidino or hexahydroazepino group substituted by the group $R_5$ wherein $R_5$ represents a 2-oxo-tetrahydrofuranyl, 2-oxo-tetrahydropyranyl, 2-oxo-1,4-dioxanyl or 2-oxo-4-($C_{1-4}$-alkyl)-morpholinyl group optionally substituted by one or two $C_{1-2}$-alkyl groups, a pyrrolidino group substituted in the 3 position by a 2-oxo-morpholino group, while the 2-oxo-morpholino group may be substituted by one or two $C_{1-2}$-alkyl groups, a piperidino or hexahydroazepino group substituted in the 3 or 4 position by a 2-oxo-morpholino group, while the 2-oxo-morpholino group may be substituted by one or two $C_{1-2}$-alkyl groups, a 4-($C_{1-4}$-alkyl)-piperazino or 4-($C_{1-4}$-alkyl)-homopiperazino group substituted at a cyclic carbon atom by $R_5$, wherein $R_5$ is as hereinbefore defined, a piperazino or homopiperazino group substituted in the 4 position by the group $R_6$, wherein $R_6$ represents a 2-oxo-tetrahydrofuran-3-yl, 2-oxo-tetrahydrofuran-4-yl, 2-oxo-tetrahydropyran-3-yl, 2-oxo-tetrahydropyran-4-yl or 2-oxo-tetrahydropyran-5-yl group optionally substituted by one or two $C_{1-2}$-alkyl groups, a pyrrolidino group substituted in the 3 position by an ($R_4NR_6$), $R_6O$, $R_6S$, $R_6SO$ or $R_6SO_2$ group, where $R_4$ and $R_6$ are as hereinbefore defined, a piperidino or hexahydroazepino group substituted in the 3 or 4 position by an ($R_4NR_6$), $R_6O$, $R_6S$, $R_6SO$ or $R_6SO_2$ group, wherein $R_4$ and $R_6$ are as hereinbefore defined, a pyrrolidino, piperidino or hexahydroazepino group substituted by an $R_5$—$C_{1-4}$-alkyl, ($R_4NR_6$)—$C_{1-4}$-alkyl, $R_6O$—$C_{1-4}$-alkyl, $R_6S$—$C_{1-4}$-alkyl, $R_6SO$—$C_{1-4}$-alkyl, $R_6SO_2$—$C_{1-4}$-alkyl or $R_4NR_6$—CO group, wherein $R_4$ to $R_6$ are as hereinbefore defined, a pyrrolidino group substituted in the 3 position by an $R_5$—CO—NR$_4$, $R_5$—$C_{1-4}$-alkylene-CONR$_4$, $(R_4NR_6)$—$C_{1-4}$-alkylene-$CONR_4$, $R_6O$—$C_{1-4}$-alkylene-$CONR_4$, $R_6S$—$C_{1-4}$-alkylene-$CONR_4$, $R_6SO$—$C_{1-4}$-alkylene-$CONR_4$, $R_6SO_2$—$C_{1-4}$-alkylene-$CONR_4$, 2-oxo-morpholino-$C_{1-4}$-alkylene-$CONR_4$, $R_5$—$C_{1-4}$-alkylene-Y or $C_{2-4}$-alkyl-Y group, where the $C_{2-4}$-alkyl moiety of the $C_{2-4}$-alkyl-Y group in each case is substituted from position 2 by an $(R_4NR_6)$, $R_6O$, $R_6S$, $R_6SO$ or $R_6SO_2$ group and the 2-oxo-morpholino moiety may be substituted by one or two $C_{1-2}$-alkyl groups, wherein $R_4$ to $R_6$ are as hereinbefore defined and Y represents an oxygen or sulphur atom, an imino, N—($C_{1-4}$-alkyl)-imino, sulphinyl or sulphonyl group, a piperidino or hexahydroazepino group substituted in the 3 or 4 position by an $R_5$—CO—$NR_4$, $R_5$—$C_{1-4}$-alkylene-$CONR_4$, $(R_4NR_6)$—$C_{1-4}$-alkylene-$CONR_4$, $R_6O$—$C_{1-4}$-alkylene-$CONR_4$, $R_6S$—$C_{1-4}$-alkylene-$CONR_4$, $R_6SO$—$C_{1-4}$-alkylene-$CONR_4$, $R_6SO_2$—$C_{1-4}$-alkylene-$CONR_4$, 2-oxo-morpholino-$C_{1-4}$-alkylene-$CONR_4$, $R_5$—$C_{1-4}$-alkylene-Y or $C_{2-4}$-alkyl-Y group, wherein Y is as hereinbefore defined, the 2-oxo-morpholino moiety may be substituted by one or two $C_{1-2}$-alkyl groups and the $C_{2-4}$-alkyl moiety of the $C_{2-4}$-alkyl-Y group is substituted in each case from position 2 by an $(R_4NR_6)$, $R_6O$, $R_6S$, $R_6SO$ or $R_6SO_2$ group, where $R_4$ to $R_6$ are as hereinbefore defined, a 4-($C_{1-4}$-alkyl)-piperazino or 4-($C_{1-4}$-alkyl)-homopiperazino group substituted at a cyclic carbon atom by an $R_5$—$C_{1-4}$-alkyl, $(R_4NR_6)$—$C_{1-4}$-alkyl, $R_6O$—$C_{1-4}$-alkyl, $R_6S$—$C_{1-4}$-alkyl, $R_6SO$—$C_{1-4}$-alkyl, $R_6SO_2$—$C_{1-4}$-alkyl or $R_4NR_6$—CO group, wherein $R_4$ to $R_6$ are as hereinbefore defined, a piperazino or homopiperazino group substituted in the 4 position by an $R_5$—$C_{1-4}$-alkyl, $R_5$—CO, $R_5$—$C_{1-4}$-alkylene-CO, $(R_4NR_6)$—$C_{1-4}$-alkylene-CO, $R_6O$—$C_{1-4}$-alkylene-CO, $R_6S$—$C_{1-4}$-alkylene-CO, $R_6SO$—$C_{1-4}$-alkylene-CO or $R_6SO_2$—$C_{1-4}$-alkylene-CO group, wherein $R_4$ to $R_6$ are as hereinbefore defined, a piperazino or homopiperazino group substituted in the 4 position by a $C_{2-4}$-alkyl group, wherein the $C_{2-4}$-alkyl group is substituted in each case from position 2 by an $(R_4NR_6)$, $R_6O$, $R_6S$, $R_6SO$ or $R_6SO_2$ group, where $R_4$ and $R_6$ are as hereinbefore defined, a pyrrolidino. piperidino or hexahydroazepino group substituted by a 2-oxo-morpholino-$C_{1-4}$-alkyl group, wherein the 2-oxo-morpholino moiety may be substituted by one or two $C_{1-2}$-alkyl groups, a pyrrolidino group substituted in the 3 position by a $C_{2-4}$-alkyl-Y group, wherein Y is as hereinbefore defined and the $C_{2-4}$-alkyl moiety of the $C_{2-4}$-alkyl-Y group is substituted in each case from position 2 by a 2-oxo-morpholino group optionally substituted by one or two $C_{1-2}$-alkyl groups, a piperidino or hexahydroazepino group substituted in the 3 or 4 position by a $C_{2-4}$-alkyl-Y group, wherein Y is as hereinbefore defined and the $C_{2-4}$-alkyl moiety of the $C_{2-4}$-alkyl-Y group is substituted in each case from position 2 by a 2-oxo-morpholino group optionally substituted by one or two $C_{1-2}$-alkyl groups, a 4-($C_{1-4}$-alkyl)-piperazino or 4-($C_{1-4}$-alkyl)-homopiperazino group substituted at a cyclic carbon atom by a 2-oxo-morpholino-$C_{1-4}$-alkyl group, wherein the 2-oxo-morpholino moiety may be substituted by one or two $C_{1-2}$-alkyl groups, a piperazino or homopiperazino group substituted in the 4 position by a 2-oxo-morpholino-$C_{1-4}$-alkylene-CO group, wherein the 2-oxo-morpholino moiety may be substituted by one or two $C_{1-2}$-alkyl groups, a piperazino or homopiperazino group substituted in the 4 position by a $C_{2-4}$-alkyl group, wherein the $C_{2-4}$-alkyl moiety is substituted in each case from position 2 by a 2-oxo-morpholino group optionally substituted by one or two $C_{1-2}$-alkyl groups, a pyrrolidinyl or piperidinyl group substituted in the 1 position by the group $R_6$, by an $R_5$—$C_{1-4}$-alkyl, $R_5$—CO, $R_5$—$C_{1-4}$-alkylene-CO, $(R_4NR_6)$—$C_{1-4}$-alkylene-CO, $R_6O$—$C_{1-4}$-alkylene $R_6S$—$C_{1-4}$-alkylene-CO, $R_6SO$—$C_{1-4}$-alkylene-CO, $R_6SO_2$—$C_{1-4}$-alkylene-CO or 2-oxo-morpholino-$C_{1-4}$-alkylene-CO group, wherein $R_4$ to $R_6$ are as hereinbefore defined and the 2-oxo-morpholino moiety may be substituted by one or two $C_{1-2}$-alkyl groups, a pyrrolidinyl or piperidinyl group substituted in the 1 position by a $C_{2-4}$-alkyl group, wherein the $C_{2-4}$-alkyl moiety is substituted in each case from position 2 by an $(R_4NR_6)$, $R_6O$, $R_6S$, $R_6SO$, $R_6SO_2$ or 2-oxo-morpholino group, where $R_4$ and $R_6$ are as hereinbefore defined and the 2-oxo-morpholino moiety may be substituted by one or two $C_{1-2}$-alkyl groups, a pyrrolidin-3-yl-$NR_4$, piperidin-3-yl-$NR_4$ or piperidin-4-yl-$NR_4$ group substituted in each case at the cyclic nitrogen atom by the group $R_6$, by an $R_5$—$C_{1-4}$-alkyl, $R_5$—CO, $R_5$—$C_{1-4}$-alkylene-CO, $(R_4NR_6)$—$C_{1-4}$-alkylene-CO, $R_6O$—$C_{1-4}$-alkylene-CO, $R_6S$—$C_{1-4}$-alkylene-CO, $R_6SO$—$C_{1-4}$-alkylene-CO, $R_6SO_2$—$C_{1-4}$-alkylene-CO or 2-oxo-morpholino-$C_{1-4}$-alkylene-CO group, wherein $R_4$ to $R_6$ are as hereinbefore defined and the 2-oxo-morpholino moiety may be substituted by one or two $C_{1-2}$-alkyl groups, a pyrrolidin-3-yl-$NR_4$, piperidin-3-yl-$NR_4$ or piperidin-4-yl-$NR_4$ group substituted in each case at the cyclic nitrogen atom by a $C_{2-4}$-alkyl group, wherein the $C_{2-4}$-alkyl moiety is substituted in each case from position 2 by an $(R_4NR_6)$, $R_6O$, $R_6S$, $R_6SO$, $R_6SO_2$ or 2-oxo-morpholino group, where $R_4$ and $R_6$ are as hereinbefore defined and the 2-oxo-morpholino moiety may be substituted by one or two $C_{1-2}$-alkyl groups, a $R_5$—$C_{1-4}$-alkylene-$NR_4$ group wherein $R_4$ and $R_5$ are as hereinbefore defined, or a $C_{2-4}$-alkyl-$NR_4$ group wherein the $C_{2-4}$-alkyl moiety is substituted in each case from position 2 by an $(R_4NR_6)$, $R_6O$, $R_6S$, $R_6SO$, $R_6SO_2$ or 2-oxo-morpholino group, where $R_4$ and $R_6$ are as hereinbefore defined and the 2-oxo-morpholino moiety may be substituted by one or two $C_{1-2}$-alkyl groups, a 2-oxo-morpholin-4-yl group substituted by the group $R_7$ or by the group $R_7$ and a $C_{1-4}$-alkyl group, where $R_7$ represents a $C_{3-4}$-alkyl, hydroxy-$C_{1-4}$-alkyl, $C_{1-4}$-alkoxy-$C_{1-4}$-alkyl, di-($C_{1-4}$-alkyl)-amino-$C_{1-4}$-alkyl, pyrrolidino-$C_{1-4}$-alkyl, piperidino-$C_{1-4}$-alkyl, morpholino-$C_{1-4}$-alkyl, 4-($C_{1-4}$-alkyl)-piperazino-$C_{1-4}$-alkyl, $C_{1-4}$-alkylsulphanyl-$C_{1-4}$-alkyl, $C_{1-4}$- alkylsulphinyl-$C_{1-4}$-alkyl, $C_{1-4}$-alkyl-sulphonyl-$C_{1-4}$-alkyl, cyano-$C_{1-4}$-alkyl, $C_{1-4}$-alkoxycarbonyl-$C_{1-4}$-alkyl, aminocarbonyl-$C_{1-4}$-alkyl, $C_{1-4}$-alkyl-aminocarbonyl-$C_{1-4}$-alkyl, di-($C_{1-4}$-alkyl)-aminocarbonyl-$C_{1-4}$-alkyl, pyrrolidinocarbonyl-$C_{1-4}$-alkyl, piperidinocarbonyl-$C_{1-4}$-alkyl, morpholinocarbonyl-$C_{1-4}$-alkyl or a 4-($C_{1-4}$-alkyl)-piperazinocarbonyl-$C_{1-4}$-alkyl group, a 2-oxo-morpholin-4-yl group substituted by two groups $R_7$, where $R_7$ is as hereinbefore defined and the two groups $R_7$ may be identical or different, a 2-oxo-morpholin-4-yl group wherein the two hydrogen atoms of a methylene group are replaced by a —$(CH_2)_m$—, —$CH_2$—Y—$CH_2$—, —$CH_2$—Y—$CH_2$—$CH_2$—, —$CH_2CH_2$—Y—$CH_2CH_2$— or —$CH_2CH_2$—Y—$CH_2CH_2CH_2$— bridge optionally substituted by one or two $C_{1-2}$-alkyl groups, where Y is as hereinbefore defined and m represents the number 2, 3, 4, 5 or 6, a 2-oxo-morpholin-4-yl group wherein a hydrogen atom in the 5 position together with a hydrogen atom in the 6 position is replaced by a —$(CH_2)_n$—, —$CH_2$—Y—$CH_2$—, —$CH_2$—Y—$CH_2CH_2$ or —$CH_2$—$CH_2$—Y—$CH_2$— bridge, where Y is as hereinbefore defined and n denotes the number 2, 3 or 4, or, if C together with D represents a group $R_c$, it may also represent a 2-oxo-morpholin-4-yl group which may be substituted by 1 to 4 $C_{1-2}$-alkyl groups, C denotes an —O—$C_{1-6}$-alkylene group, where the alkylene moiety is linked to the group D, or an oxygen atom, while this may not be linked to a nitrogen atom of the group D, and D denotes an amino group substituted by 2 $C_{1-4}$-alkyl groups wherein the alkyl groups may be identical or different and each alkyl moiety may be substituted from position 2 by a $C_{1-4}$-alkoxy or di-($C_{1-4}$-alkyl)-amino group or by a 4- to 7-membered alkyleneimino group, while in the abovementioned 6- or 7-membered alkyleneimino groups a methylene group in each case may be replaced in the 4 position by an oxygen or sulphur atom of by a sulphinyl, sulphonyl or N—($C_{1-4}$alkyl)-imino group, a 4- or 7-membered alkyleneimino group optionally substituted by 1 to 4 methyl group, a 6- to 7-membered alkyleneimino group optionally substituted by 1 to 2 methyl group where in each case a methylene group in the 4 position is replaced by an oxygen of sulphur atom, by a sulphinyl, sulphonyl, or N—($C_{1-4}$-alkyl)-imino group, an imidazolyl group optionally substituted by 1 to 3 methyl group, a $C_{5-7}$-cycloalkyl group wherein a methylene group is replaced by an oxygen or sulphur atom, by a sulphinyl, sulphonyl or N—($C_{1-4}$-alkyl)-imino group, or C together with D denotes a hydrogen atom, a $C_{1-6}$-alkoxy group optionally substituted from position 2 by a hydroxy or $C_{1-4}$-alkyl group, a $C_{3-7}$-cycloalkoxy or $C_{3-7}$-cycloalkyl-$C_{1-4}$-alkoxy group, a tetrahydrofuran-3-yloxy, tetrahydropyran-3-yloxy, tetrahydropyran-4-yloxy, tetrahydrofuranylmethoxy or tetrahydropyranylmethoxy group, or a group $R_c$, where $R_c$ denotes a $C_{2-6}$-alkoxy group which is substituted from position 2 by a $C_{4-7}$-cycloalkoxy or $C_{3-7}$-cycloalkyl-$C_{1-3}$-alkoxy group, a $C_{4-7}$-cycloalkoxy or $C_{3-7}$-cycloalkyl-$C_{1-6}$-alkoxy group, wherein the cycloalkyl moiety is substituted in each case by a $C_{1-4}$-alkyl, $C_{1-4}$-alkoxy, di-($C_{1-4}$-alkyl)-amino, pyrrolidino, piperidino, morpholino, piperazino, N—($C_{1-2}$-alkyl)-piperazino, $C_{1-4}$-alkoxy-$C_{1-2}$-alkyl, di-($C_{1-4}$-alkyl)-amino-$C_{1-2}$-alkyl, pyrrolidino-$C_{1-2}$-alkyl, piperidino-$C_{1-2}$-alkyl, morpholino-$C_{1-2}$-alkyl, piperazino-$C_{1-2}$-alkyl or N—($C_{1-2}$-alkyl)-piperazino-$C_{1-2}$-alkyl group, where the abovementioned cycloalkyl moieties may additionally be substituted by a methyl or ethyl group, while, unless stated otherwise, the aryl moieties mentioned in the definition of the abovementioned groups denote a phenyl group which may be mono- or disubstituted by R', while the substituents may be identical or different, and R' represents a fluorine, chlorine, bromine or iodine atom, a $C_{1-2}$-alkyl, trifluoromethyl or $C_{1-2}$-alkoxy group, or wherein if a phenyl group is disubstituted by R' and the two groups R' are bound to adjacent carbon atoms of the phenyl group then the two groups R' may together denote a $C_{3-4}$-alkylene, methylenedioxy or 1,3-butadien-1,4-ylene group, or a tautomer or salt thereof.

2. A compound of the formula I according to claim 1 wherein

X denotes a nitrogen atom, $R_a$ denotes a hydrogen atom, $R_b$ denotes a 1-phenylethyl, 3-methylphenyl, 3-chlorophenyl, 3-bromophenyl or 3-chloro-4-fluorophenyl group, $R_c$ denotes an —A—B group wherein A denotes a —$OCH_2CH_2$, —$OCH_2CH_2CH_2$ or —$OCH_2CH_2CH_2CH_2$ group, where the alkylene moiety in each case is linked to the group B, and B denotes a piperidino group wherein the two hydrogen atoms in the 4 position are replaced by a —$CH_2$—O—CO—$CH_2$, —$CH_2CH_2$—O—CO, —$CH_2CH_2$—O—CO—$CH_2$, —O—CO—$CH_2$—$NCH_3$—$CH_2$ or —O—CO—$CH_2$—O—$CH_2$— bridge, a piperazino group wherein a hydrogen atom in the 3 position together with the hydrogen atom in the 4 position are replaced by a —CO—O—$CH_2$—$CH_2$ or —$CH_2$—O—CO—$CH_2$— bridge, where in each case the left-hand end of the abovementioned bridges is bound to the 3 position of the piperazino ring, a piperidino group which is substituted in the 4 position by a 2-oxo-morpholino or 2-oxo-morpholinomethyl group, where the 2-oxo-morpholino moiety may be substituted in each case by one or two methyl groups, a piperazino group which is substituted in the 4 position by a 2-oxo-tetrahydrofuran-3-yl or 2-oxo-tetrahydrofuran-4-yl group, a piperidino group which is substituted in the 4 position by an $R_6S$ group, where $R_6$ denotes a 2-oxo-tetrahydrofuran-3-yl or 2-oxo-tetrahydrofuran-4-yl group, a piperazino group which is substituted in the 4 position by a 2-oxo-tetrahydrofuranylmethyl or 2-oxo-tetrahydrofuranylcarbonyl group, a piperazino group which is substituted in the 4 position by a [2-(2-oxo-tetrahydrofuran-3-ylsulphenyl)ethyl] group, a piperidin-4-yl group which is substituted in the 1 position by a 2-oxo-tetrahydrofuran-3-yl or 2-oxo-tetrahydrofuran-4-yl group, a 2-oxo-morpholin-4-yl group which is substituted by a methoxymethyl or methoxyethyl group, a 2-oxo-morpholin-4-yl group wherein the two hydrogen atoms of a methylene group are replaced by a —CH$_2$CH$_2$CH$_2$CH$_2$, —CH$_2$CH$_2$CH$_2$CH$_2$CH$_2$, —CH$_2$—O—CH$_2$CH$_2$ or —CH$_2$CH$_2$—O—CH$_2$CH$_2$— bridge, and R$_d$ represents a methoxy, cyclopropylmethoxy, tetrahydrofuran-3-yloxy, tetrahydropyran-3-yloxy, tetrahydropyran-4-yloxy, tetrahydrofuranylmethoxy or tetrahydropyranylmethoxy group, or a tautomer or salt thereof.

3. A compound of the formula I according to claim 1 wherein

X denotes a nitrogen atom,

R$_a$ denotes a hydrogen atom,

R$_b$ denotes a 1-phenylethyl, 3-methylphenyl, 3-chlorophenyl, 3-bromophenyl or 3-chloro-4-fluorophenyl group, R$_c$ denotes a methoxy, cyclopentyloxy, cyclopropylmethoxy, cyclopentylmethoxy, tetrahydrofuran-3-yloxy, tetrahydropyran-3-yloxy, tetrahydropyran-4-yloxy, tetrahydrofuranylmethoxy or tetrahydropyranylmethoxy group and R$_d$ denotes an —A—B group wherein A denotes an —OCH$_2$CH$_2$, —OCH$_2$CH$_2$CH$_2$ or —OCH$_2$CH$_2$CH$_2$CH$_2$ group, where the alkylene moiety in each case is linked to the group B, and B denotes a piperidino group wherein the two hydrogen atoms in the 4 position are replaced by a —CH$_2$—O—CO—CH$_2$, —CH$_2$CH$_2$—O—CO, —CH$_2$CH$_2$—O—CO—CH$_2$, —O—CO—CH$_2$—NCH$_3$—CH$_2$ or —O—CO—CH$_2$—O—CH$_2$— bridge, a piperazino group wherein a hydrogen atom in the 3 position together with the hydrogen atom in the 4 position are replaced by a —CO—O—CH$_2$—CH$_2$ or —CH$_2$—O—CO—CH$_2$— bridge, where in each case the left-hand end of the abovementioned bridges is bound to the 3 position of the piperazino ring, a piperidino group which is substituted in the 4 position by a 2-oxo-morpholino or 2-oxo-morpholinomethyl group, while the 2-oxo-morpholino moiety may be substituted in each case by one or two methyl groups, a piperazino group which is substituted in the 4 position by a 2-oxo-tetrahydrofuran-3-yl or 2-oxo-tetrahydrofuran-4-yl group, a piperidino group which is substituted in the 4 position by an R$_6$S group, where R$_6$ represents a 2-oxo-tetrahydrofuran-3-yl or 2-oxo-tetrahydrofuran-4-yl group, a piperazino group which is substituted in the 4 position by a 2-oxo-tetrahydrofuranylmethyl or 2-oxo-tetrahydrofuranylcarbonyl group, a piperazino group which is substituted in the 4 position by a [2-(2-oxo-tetrahydrofuran-3-ylsulphenyl)ethyl] group, a piperidin-4-yl group which is substituted in the 1 position by a 2-oxo-tetrahydrofuran-3-yl or 2-oxo-tetrahydrofuran-4-yl group, a 2-oxo-morpholin-4-yl group which is substituted by a methoxymethyl or methoxyethyl group, a 2-oxo-morpholin-4-yl group wherein the two hydrogen atoms of a methylene group are replaced by a —CH$_2$CH$_2$CH$_2$CH$_2$, —CH$_2$CH$_2$CH$_2$CH$_2$CH$_2$, —CH$_2$—O—CH$_2$CH$_2$ or —CH$_2$CH$_2$—O—CH$_2$CH$_2$— bridge, or a tautomer or salt thereof.

4. A compound of the formula I according to claim 1 wherein

X denotes a nitrogen atom,

R$_a$ denotes a hydrogen atom,

R$_b$ denotes a 3-chloro-4-fluorophenyl group,

R$_c$ denotes a cyclopentyloxy, cyclopropylmethoxy, cyclopentylmethoxy, tetrahydrofuran-3-yloxy or tetrahydrofuran-2-yl-methoxy group and R$_d$ denotes an —A—B group wherein A denotes a —OCH$_2$CH$_2$ group, where the alkylene moiety is linked to the group B, and B denotes a piperazino group wherein a hydrogen atom in the 3 position together with the hydrogen atom in the 4 position is replaced by a —CH$_2$—O—CO—CH$_2$— bridge, while the left-hand end of the abovementioned bridge is bound to the 3 position of the piperazino ring, a piperazino group which is substituted in the 4 position by a 2-oxo-tetrahydrofuran-3-yl, 2-oxo-tetrahydrofuran-4-yl-,2-oxo-tetrahydrofuranylmethyl or 2-oxo-tetrahydrofuranylcarbonyl group, or a tautomer or salt thereof.

5. A compound selected from the group consisting of:

(1) 4-[(3-chloro-4-fluorophenyl)amino]-6-cyclopentylmethoxy-7-{2-[4-(2-oxo-tetrahydrofuran-4-yl)-piperazin-1-yl]-ethoxy}-quinazoline.

(2) 4-[(3-chloro-4-fluorophenyl)amino]-6-cyclopentyloxy-7-{2-[4-(2-oxo-tetrahydrofuran-4-yl)-piperazin-1-yl]-ethoxy}-quinazoline, (3) 4-[(3-chloro-4-fluorophenyl)amino]-6-cyclopropylmethoxy-7-{2-[4-(2-oxo-tetrahydrofuran-4-yl)-piperazin-1-yl]-ethoxy)}-quinazoline and (4) 4-[(3-chloro-4-fluorophenyl)amino]-6-cyclopropylmethoxy-7-(2-{4-[(R)-(2-oxo-tetrahydrofuran-5-yl)methyl]-piperazin-1-yl}-ethoxy)-quinazoline, or a tautomer or salts thereof.

6. A physiologically acceptable salt of a compound according to claim 1, 2, 3, 4 or 5, formed with an inorganic or organic acid or base.

7. A pharmaceutical composition comprising a compound according to claim 1, 2, 3, 4 or 5 or a pharmaceutically acceptable salt thereof and a pharmaceutically acceptable carrier or diluent.

8. A method of treating a benign or malignant tumour which comprises administering a therapeutically effective amount of a compound according claim 1, 2, 3, 4 or 5 or a pharmaceutically acceptable salt thereof.

* * * * *